(12) United States Patent
Zhang et al.

(10) Patent No.: US 11,345,663 B2
(45) Date of Patent: May 31, 2022

(54) COMPOUND AND DISPLAY PANEL CONTAINING THE SAME

(71) Applicant: Wuhan Tianma Micro-electronics Co., Ltd., Wuhan (CN)

(72) Inventors: Lei Zhang, Wuhan (CN); Wei Gao, Wuhan (CN); Qing Zhu, Wuhan (CN); Jinghua Niu, Wuhan (CN); Ping An, Wuhan (CN); Yan Lu, Wuhan (CN); Hongyan Zhu, Wuhan (CN); Gaojun Huang, Wuhan (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 399 days.

(21) Appl. No.: 16/372,443

(22) Filed: Apr. 2, 2019

(65) Prior Publication Data

US 2020/0207714 A1    Jul. 2, 2020

(30) Foreign Application Priority Data

Dec. 28, 2018    (CN) .......................... 201811622639.8

(51) Int. Cl.
*C07D 209/86*    (2006.01)
*C07D 213/38*    (2006.01)
(Continued)

(52) U.S. Cl.
CPC ......... *C07D 209/86* (2013.01); *C07D 213/38* (2013.01); *C07D 213/74* (2013.01);
(Continued)

(58) Field of Classification Search
CPC .. C07D 209/86; C07D 213/38; C07D 213/74; C07D 239/26; C07D 239/42;
(Continued)

(56) References Cited

U.S. PATENT DOCUMENTS 8,698,395 B2 * 4/2014 Im .................. H01L 51/5275
313/512
2016/0308162 A1 * 10/2016 Yoo ..................... H01L 27/3244

FOREIGN PATENT DOCUMENTS

CN    108947889 A    12/2018
CN    111052428 A    4/2020
(Continued)

OTHER PUBLICATIONS

Computer-generated English-language translation of KR-20170111802-A.*

(Continued)

*Primary Examiner* — Vu A Nguyen
(74) *Attorney, Agent, or Firm* — Kilpatrick Townsend & Stockton, LLP

(57) ABSTRACT

The present disclosure provides a compound used as the CPL material. The compound has a structure as shown in chemical formula I,

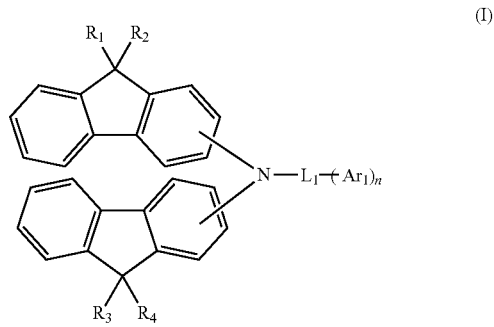

in which $L_1$ is selected from the group consisting of a substituted or unsubstituted C6-C30 arylene, C3-C30 het-
(Continued)

eroarylene, a substituted or unsubstituted C10-C60 fused arylene, and a substituted or unsubstituted C10-C60 fused heteroarylene; $Ar_1$ is selected from the group consisting of a substituted or unsubstituted C6-C30 arylene, C3-C30 heteroarylene, a substituted or unsubstituted C10-C60 fused arylene, and a substituted or unsubstituted C10-C60 fused heteroarylene; n is 1 or 2, and when n is 2, the two $Ar_1$ are identical or different; $R_1$, $R_2$, $R_3$ and $R_4$ are each independently selected from the group consisting of hydrogen, and a substituted or unsubstituted aryl or fused aryl, $R_1$ and $R_2$ are optionally bonded to form a ring, and $R_3$ and $R_4$ are optionally bonded to form a ring.

10 Claims, 2 Drawing Sheets

(51) Int. Cl.

| | | |
|---|---|---|
| *C07D 213/74* | (2006.01) | |
| *C07D 239/26* | (2006.01) | |
| *C07D 239/42* | (2006.01) | |
| *C07D 307/91* | (2006.01) | |
| *C07D 333/76* | (2006.01) | |
| *C07D 401/14* | (2006.01) | |
| *C07D 403/14* | (2006.01) | |
| *C07D 409/14* | (2006.01) | |
| *C07D 471/04* | (2006.01) | |
| *H01L 51/00* | (2006.01) | |
| *H01L 51/50* | (2006.01) | |
| *H01L 51/52* | (2006.01) | |

(52) U.S. Cl.
CPC ......... *C07D 239/26* (2013.01); *C07D 239/42* (2013.01); *C07D 307/91* (2013.01); *C07D 333/76* (2013.01); *C07D 401/14* (2013.01); *C07D 403/14* (2013.01); *C07D 409/14* (2013.01); *C07D 471/04* (2013.01); *H01L 51/006* (2013.01); *H01L 51/0058* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/5004* (2013.01); *H01L 51/5253* (2013.01); *H01L 51/5056* (2013.01); *H01L 51/5072* (2013.01)

(58) Field of Classification Search
CPC .. C07D 307/91; C07D 333/76; C07D 401/14; C07D 403/14; C07D 409/14; C07D 471/04; H01L 51/006; H01L 51/0061
See application file for complete search history.

(56) References Cited

FOREIGN PATENT DOCUMENTS

| | | | |
|---|---|---|---|
| CN | 111918950 A | | 11/2020 |
| KR | 20130096334 A | | 8/2013 |
| KR | 20170111802 A | * | 10/2017 |
| KR | 20170111802 A | | 10/2017 |
| KR | 20170136391 A1 | | 12/2017 |
| KR | 20180084423 A | | 7/2018 |
| KR | 20180131115 A | * | 12/2018 |
| WO | 2016105138 A2 | | 6/2016 |

OTHER PUBLICATIONS

Computer-generated English-language translation of KR-20180131115-A.*
Doctoral thesis by Walter J. Finkenzeller of the University of Regensburg, Germany, 2008 (the first 30 pages).*
Office Action of CN Patent Application No. 201811622639.8 dated Apr. 9, 2021.
Office Action of CN Patent Application No. 201811622639.8 dated Sep. 10, 2021.

* cited by examiner

COMPOUND AND DISPLAY PANEL CONTAINING THE SAME

CROSS-REFERENCE TO RELATED APPLICATIONS

The present disclosure claims priority to Chinese Patent Application No. 201811622639.8, filed on Dec. 28, 2018, the content of which is incorporated herein by reference in its entirety.

FIELD

The present disclosure relates to the field of organic electroluminescent materials, and particularly, to a difluorenylamine compound, and a display panel containing the difluorenylamine compound.

BACKGROUND

The organic light-emitting diode (OLED) has made great progress with the development in decades. Although an internal quantum efficiency of OLED is already close to 100%, an external quantum efficiency thereof is still only about 20%. Most light emitted by OLED is confined inside the light-emitting device due to factors such as substrate mode loss, surface plasma and waveguide effect, resulting in a large amount of energy loss.

In a top-emission type device, an organic capping layer (CPL) is deposited on a translucent metal aluminum electrode to adjust an optical interference distance, suppress external light reflection, and inhibit extinction caused by surface plasma energy movement, thereby improving the light extraction efficiency and the luminous efficiency of OLED devices.

OLED has very high requirements on the properties of CPL materials: no absorption in the visible wavelength region (400-700 nm), a high refractive index (generally greater than 2.1), a small extinction coefficient (smaller than 0.00) in the wavelength range of 400-600 nm, a high glass transition temperature, and molecular thermal stability (high glass transition temperature, while allowing deposition without thermal decomposition).

Existing CPL materials are mostly aromatic amine derivatives, phosphoxy derivatives and quinolinone derivatives, which have function of hole transmission and electron transmiassion, and can improve the light extraction efficiency to some extent. However, the existing CPL materials generally have a refractive index below 1.9, which cannot meet the requirements on high refractive index. In the meantime, the use of the amine derivative of a specific structure having a high refractive index and materials conforming to specific parameters did improve the light extraction efficiency, but failed to solve the problem of luminous efficiency (especially for blue light-emitting elements). The molecular structure of the material known in the prior art, which is designed to increase the molecular density and achieve high thermal stability, is too large and loose to be closely packed. In this way, a large amount of gel holes will be generated during deposition, leading to a poor covering tightness. Therefore, it is necessary to develop a new type of CPL material to improve the performance of the OLED devices.

SUMMARY

Embodiments of the present disclosure provides a compound having a structure as shown in chemical formula I:

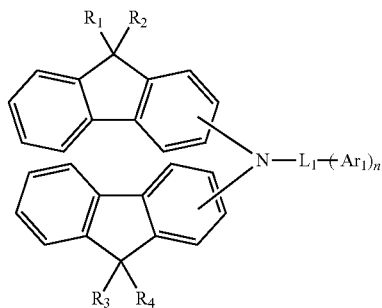

chemical formula I in which $L_1$ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene;

$Ar_1$ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene;

n is 1 or 2, and when n is 2, the two An are identical or different; and $R_1$, $R_2$, $R_3$ and $R_4$ are each independently selected from the group consisting of hydrogen, and a substituted or unsubstituted aryl or fused aryl, $R_1$ and $R_2$ are bonded together to form a ring, and $R_3$ and $R_4$ are bonded together to form a ring.

Another embodiment of the present disclosure provides a display panel including an organic light-emitting device. The organic light-emitting device includes an anode, a cathode disposed oppositely to the anode, a capping layer disposed at a side of the cathode facing away from anode, and an organic layer disposed between the anode and the cathode. The organic layer includes an electron transmission layer, a hole transmission layer and a light-emitting layer, and the capping layer. The capping layer contains the compound according to one embodiment.

aspect further embodiment of the present disclosure provides a display panel including an organic light-emitting device. The organic light-emitting device includes an anode, a cathode disposed oppositely to the anode, a capping layer disposed at a side of the cathode facing away from anode, and an organic layer disposed between the anode and the cathode. The organic layer includes an electron transmission layer, a hole transmission layer and a light-emitting layer, and the capping layer disposed between the electron transmission layer and the hole transmission layer. The electron transmission layer or the hole transmission layer contains the compound according to one embodiment.

DESCRIPTION OF EMBODIMENTS

Figure 1:
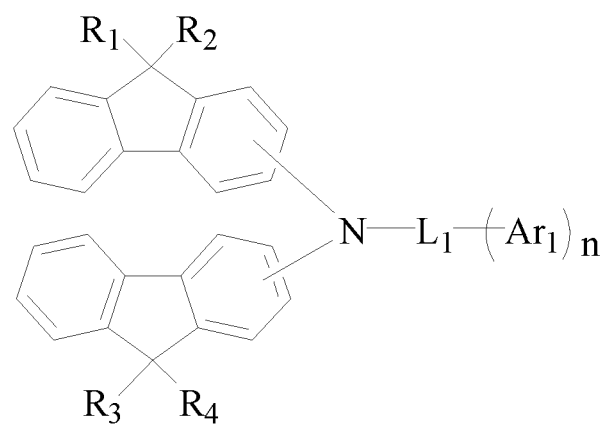
FIG. 1 is a chemical formula of a compound according to an embodiment of the present disclosure.

The present disclosure is further described with the following embodiments and comparative examples. These embodiments are only intended to illustrate the present disclosure, but not to limit the present disclosure.

In one embodiment of the present disclosure, a compound having a structure as shown in chemical formula I is provided:

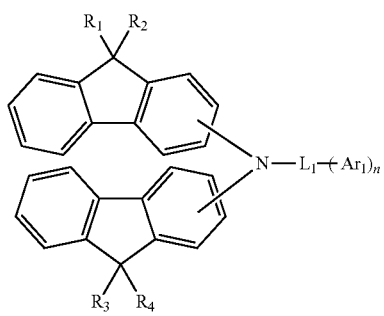

chemical formula I in which $L_1$ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene;

$Ar_1$ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene;

n is 1 or 2, and when n is 2, the two $Ar_1$ are identical or different; and $R_1$, $R_2$, $R_3$ and $R_4$ are each independently selected from the group consisting of hydrogen, and a substituted or unsubstituted aryl or fused aryl, $R_1$ and $R_2$ are bonded together to form a ring, and $R_3$ and $R_4$ are bonded together to form a ring.

The compound of the present disclosure has a high refractive index, and can effectively improve the external quantum efficiency (EQE) of an organic light-emitting device when used as the material of the capping layer of the organic light-emitting device. In addition, the compound of the present disclosure has a lower extinction efficiency in the blue light region (400-450 nm), and thus has nearly no absorption of blue light, thereby further improving the luminous efficiency.

According to an embodiment of the compound of the present disclosure, the chemical formula I can be any structure as shown in chemical formula I-1 to chemical formula 1-6:

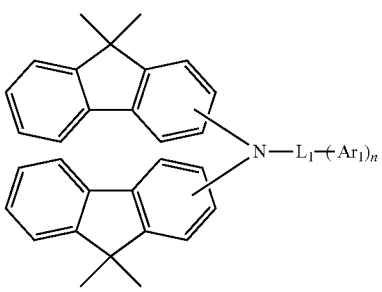

chemcial formula I-1

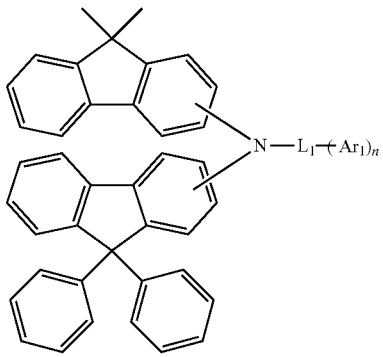

chemical formula I-2

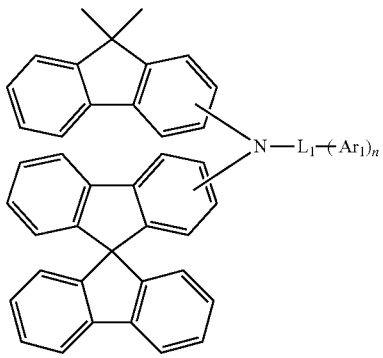

chemical formula I-3

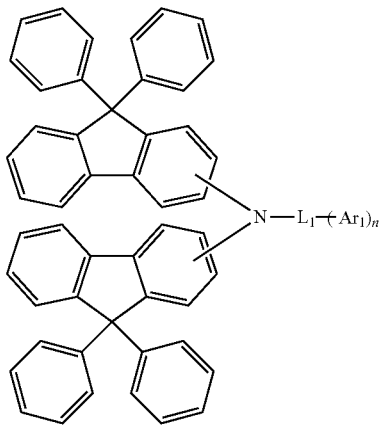

chemical formula I-4

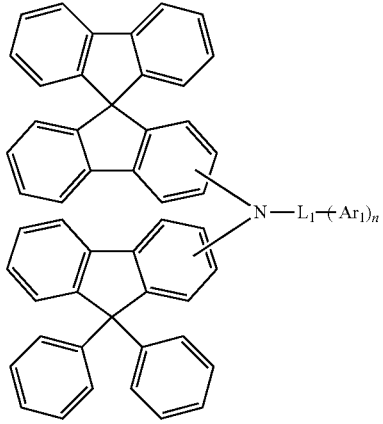

chemical formula I-5 chemical formula I-6

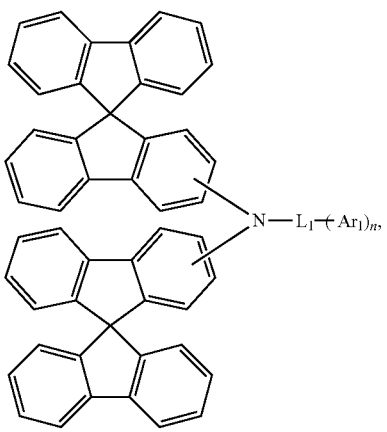

L₁ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene;

Ar₁ is selected from the group consisting of a substituted or unsubstituted C6-C30 arylene, a substituted or unsubstituted C3-C30 heteroarylene, a substituted or unsubstituted C10-C60 fused arylene, and a substituted or unsubstituted C10-C60 fused heteroarylene; and n is 1 or 2, and when n is 2, the two Ar₁ are identical or different.

According to an embodiment of the compound of the present disclosure, L₁ is selected from the groups as shown in chemical formula 2-1 to chemical formula 2-32:

chemical formula 2-1

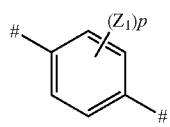

chemical formula 2-2

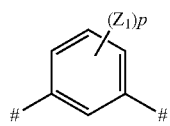

chemical formula 2-3

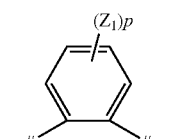

chemical formula 2-4

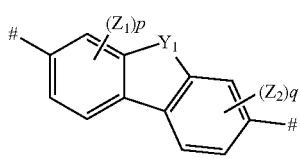

chemical formula 2-5

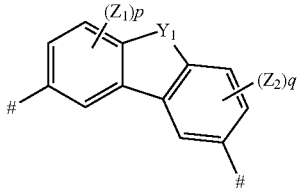

chemical formula 2-6

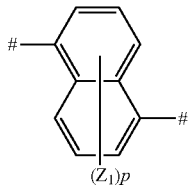

chemical formula 2-7

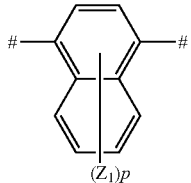

chemical formula 2-8

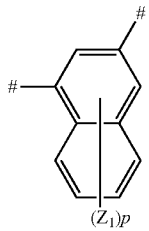

chemical formula 2-9

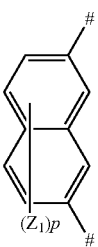

chemical formula 2-10

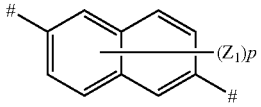

chemical formula 2-11

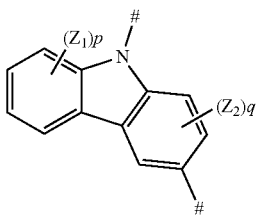

chemical formula 2-12

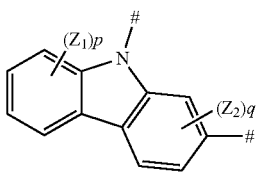

chemical formula 2-13
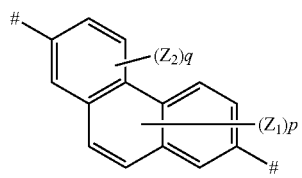
chemical formula 2-14
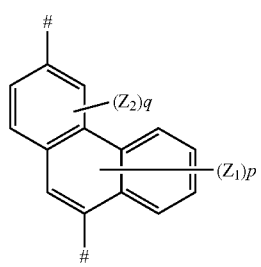
chemical formula 2-15
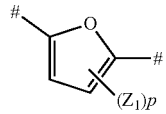
chemical formula 2-16
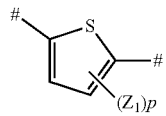
chemical formula 2-17
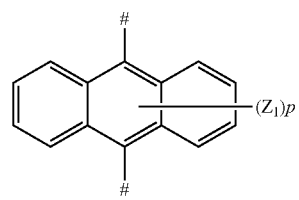
chemical formula 2-18
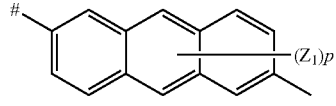
chemical formula 2-19
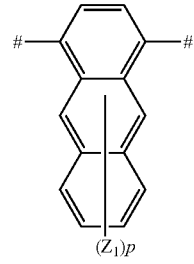
chemical formula 2-20
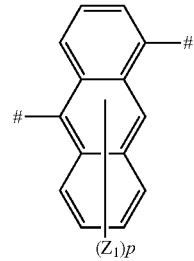
chemical formula 2-21
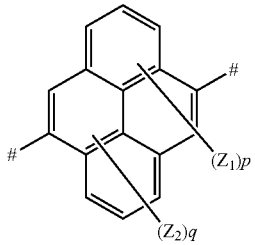
chemical formula 2-22
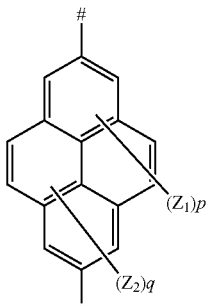
chemical formula 2-23
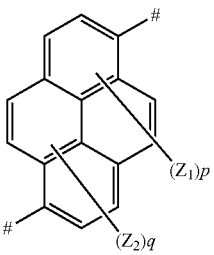
chemical formula 2-24
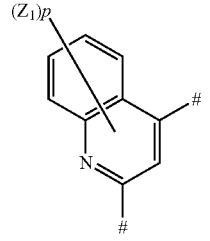
chemical formula 2-25
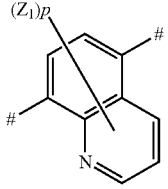
chemical formula 2-26
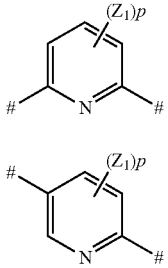
chemical formula 2-27

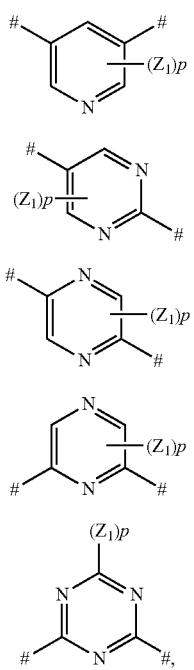

chemical formula 2-28 chemical formula 2-29 chemical formula 2-30 chemical formula 2-31 chemical formula 2-32

$Z_1$ and $Z_2$ are each independently selected from the group consisting of hydrogen, a substituted or unsubstituted C6-C18 aryl, a substituted or unsubstituted pyridyl, a substituted or unsubstituted quinolyl, a substituted or unsubstituted C1-C16 alkyl, a substituted or unsubstituted C1-C16 alkoxy, hydroxyl, and carboxyl;

p and q are each an integer independently selected from 0 to 5;

$Y_1$ is S or O; and # represents a bonding position.

According to an embodiment of the compound of the present disclosure, $L_1$ is selected from the groups as shown in chemical formula 3-1 to chemical formula 3-24:

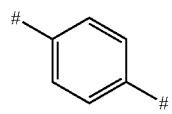

chemical formula 3-1

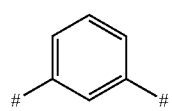

chemical formula 3-2

chemical formula 3-3

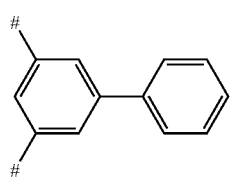

chemical formula 3-4

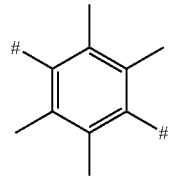

chemical formula 3-5

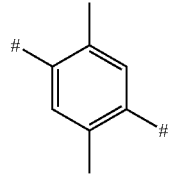

chemical formula 3-6

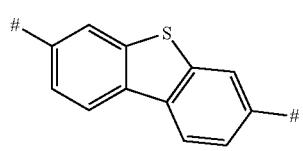

chemical formula 3-7

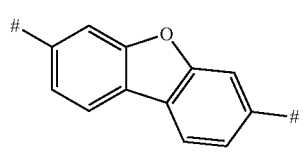

chemical formula 3-8

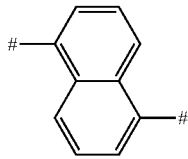

chemical formula 3-9

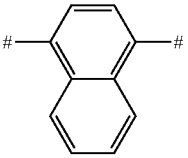

chemical formula 3-10

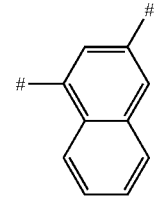

chemical formula 3-11

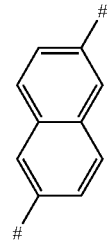

chemical formula 3-12

-continued chemical formula 3-13
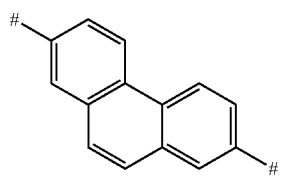

chemical formula 3-14
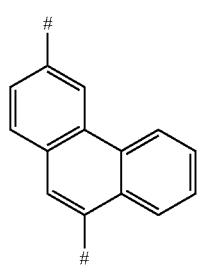

chemical formula 3-15
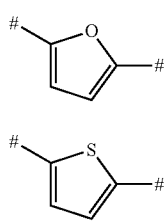

chemical formula 3-16
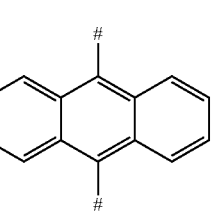

chemical formula 3-17
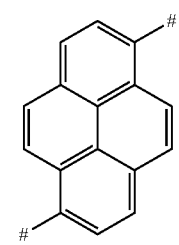

chemical formula 3-18
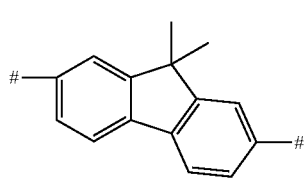

chemical formula 3-19
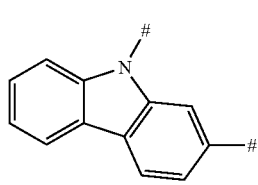

chemical formula 3-20
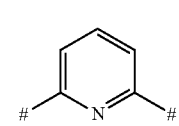

chemical formula 3-21
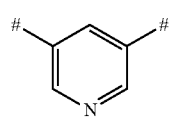

chemical formula 3-22
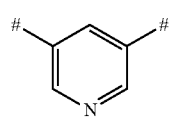

chemical formula 3-23
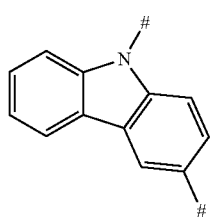

chemical formula 3-24
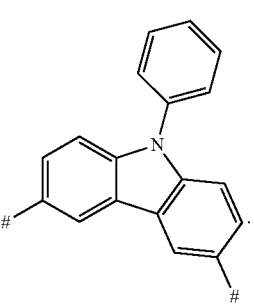

According to an embodiment of the compound of the present disclosure, $Ar_1$ is selected from the groups as shown in chemical formula 4-1 to chemical formula 4-29:

chemical formula 4-1
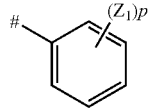

chemical formula 4-2
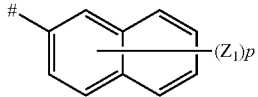

chemical formula 4-3
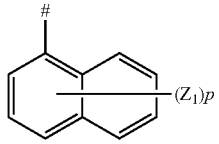

chemical formula 4-4
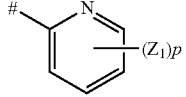

chemical formula 4-5
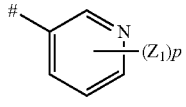

chemical formula 4-6
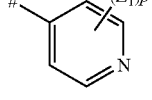

-continued chemical formula 4-7 chemical formula 4-8 chemical formula 4-9 chemical formula 4-10 chemical formula 4-11 chemical formula 4-12 chemical formula 4-13 chemical formula 4-14 chemical formula 4-15 chemical formula 4-16

-continued chemical formula 4-17 chemical formula 4-18 chemical formula 4-19 chemical formula 4-20 chemical formula 4-21 chemical formula 4-22 chemical formula 4-23 chemical formula 4-24

-continued chemical formula 4-25
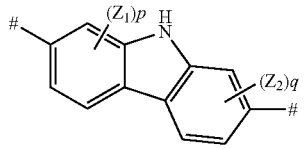

chemical formula 4-26
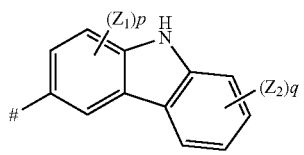

chemical formula 4-27
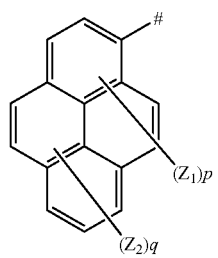

chemical formula 4-28
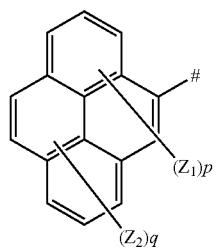

chemical formula 4-29
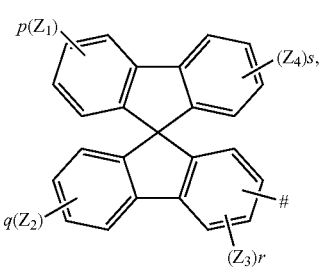

$Z_1$, $Z_2$, $Z_3$ and $Z_4$ are each independently selected from the group consisting of hydrogen, a substituted or unsubstituted C6-C18 aryl, a substituted or unsubstituted pyridyl, a substituted or unsubstituted quinolyl, a substituted or unsubstituted C1-C16 alkyl, a substituted or unsubstituted C1-C16 alkoxy, hydroxyl, carboxyl, cyano, and halogen;

p, q, s and r are each an integer independently selected from 0 to 5;

$Y_2$ is S or O; and # represents a bonding position.

According to an embodiment of the compound of the present disclosure, $Ar_1$ is selected from the groups as shown in chemical formula 5-1 to chemical formula 5-41:

chemical formula 5-1
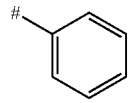

chemical formula 5-2
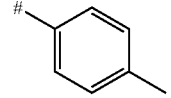

chemical formula 5-3
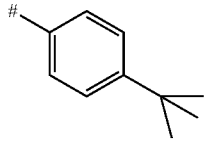

chemical formula 5-4
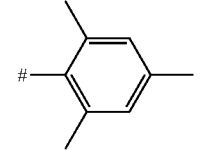

chemical formula 5-5
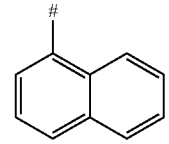

chemical formula 5-6
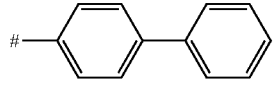

chemical formula 5-7
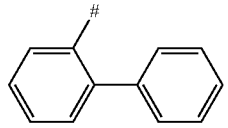

chemical formula 5-8
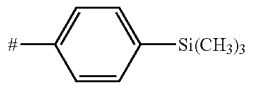

chemical formula 5-9
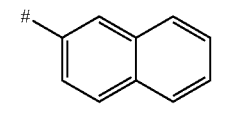

chemical formula 5-10
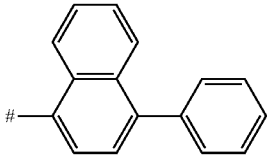

chemical formula 5-11
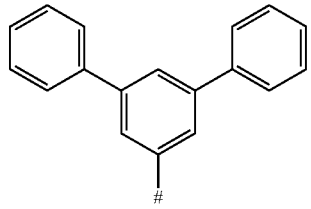

-continued
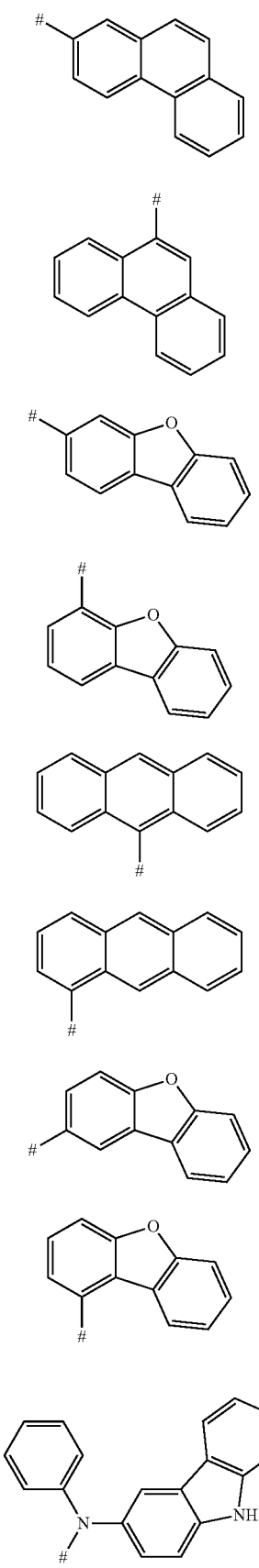
chemical formula 5-12
chemical formula 5-13
chemical formula 5-14
chemical formula 5-15
chemical formula 5-16
chemical formula 5-17
chemical formula 5-18
chemical formula 5-19
chemical formula 5-20
-continued
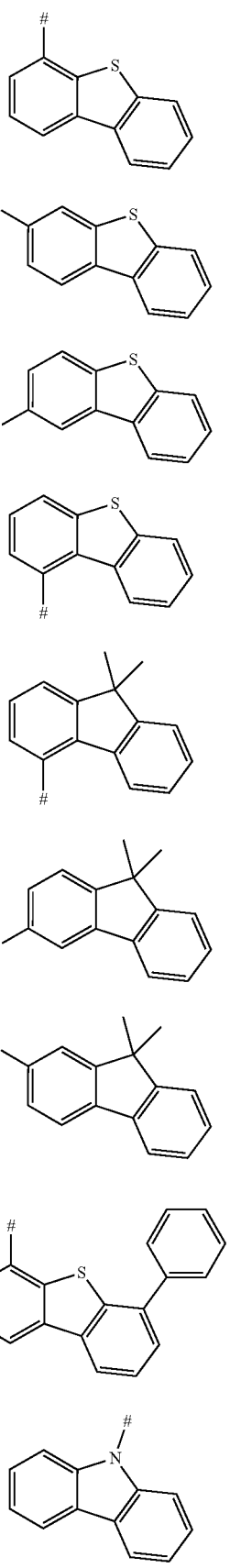
chemical formula 5-21
chemical formula 5-22
chemical formula 5-23
chemical formula 5-24
chemical formula 5-25
chemical formula 5-26
chemical formula 5-27
chemical formula 5-28
chemical formula 5-29 chemical formula 5-30
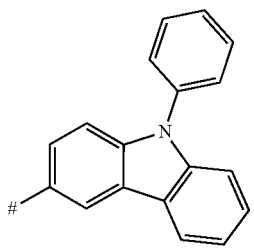

chemical formula 5-31
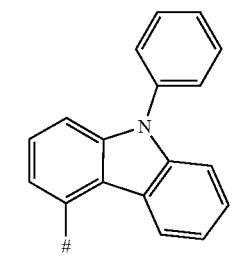

chemical formula 5-32
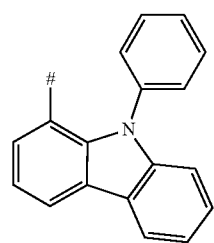

chemical formula 5-33
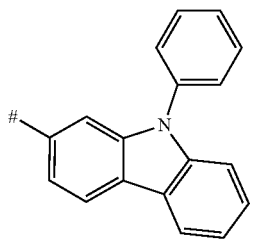

chemical formula 5-34
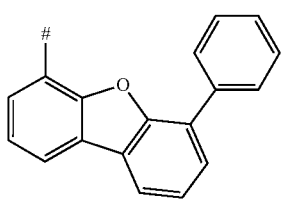

chemical formula 5-35
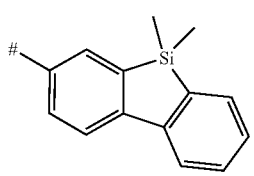

chemical formula 5-36
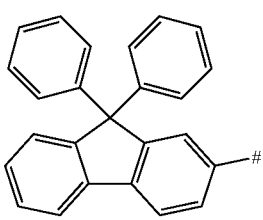

chemical formula 5-37
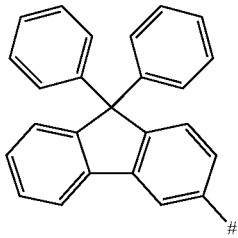

chemical formula 5-38
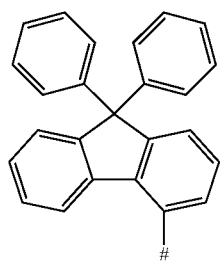

chemical formula 5-39
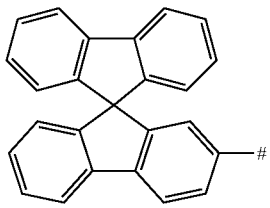

chemical formula 5-40
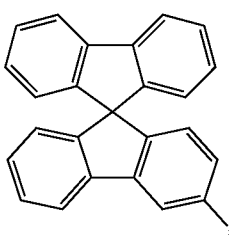

chemical formula 5-41
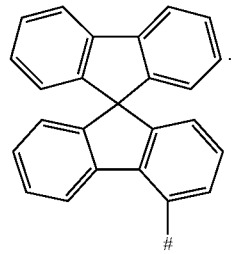

According to an embodiment of the compound of the present disclosure, $Ar_1$ is selected from the groups as shown in chemical formula 6-1 to chemical formula 6-18:

chemical formula 6-1
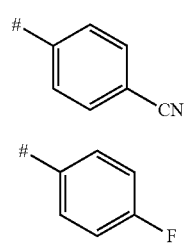

chemical formula 6-2
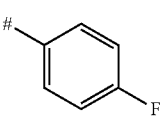

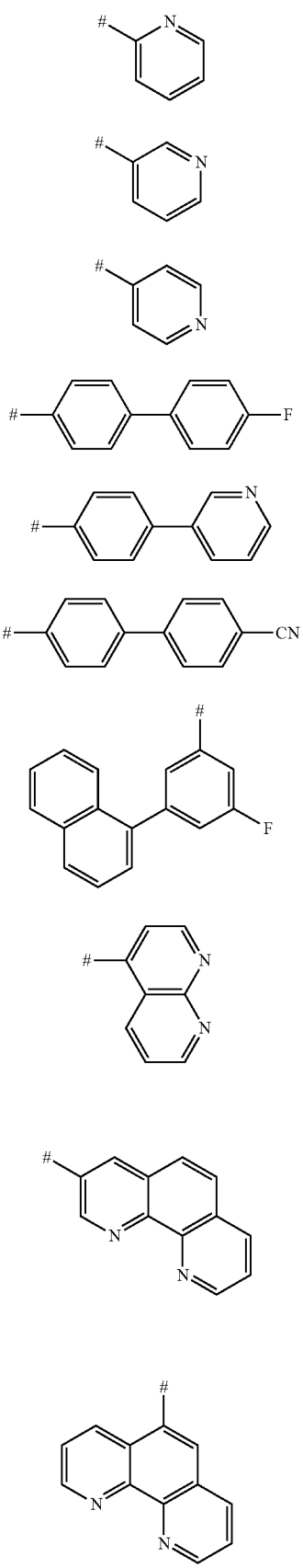
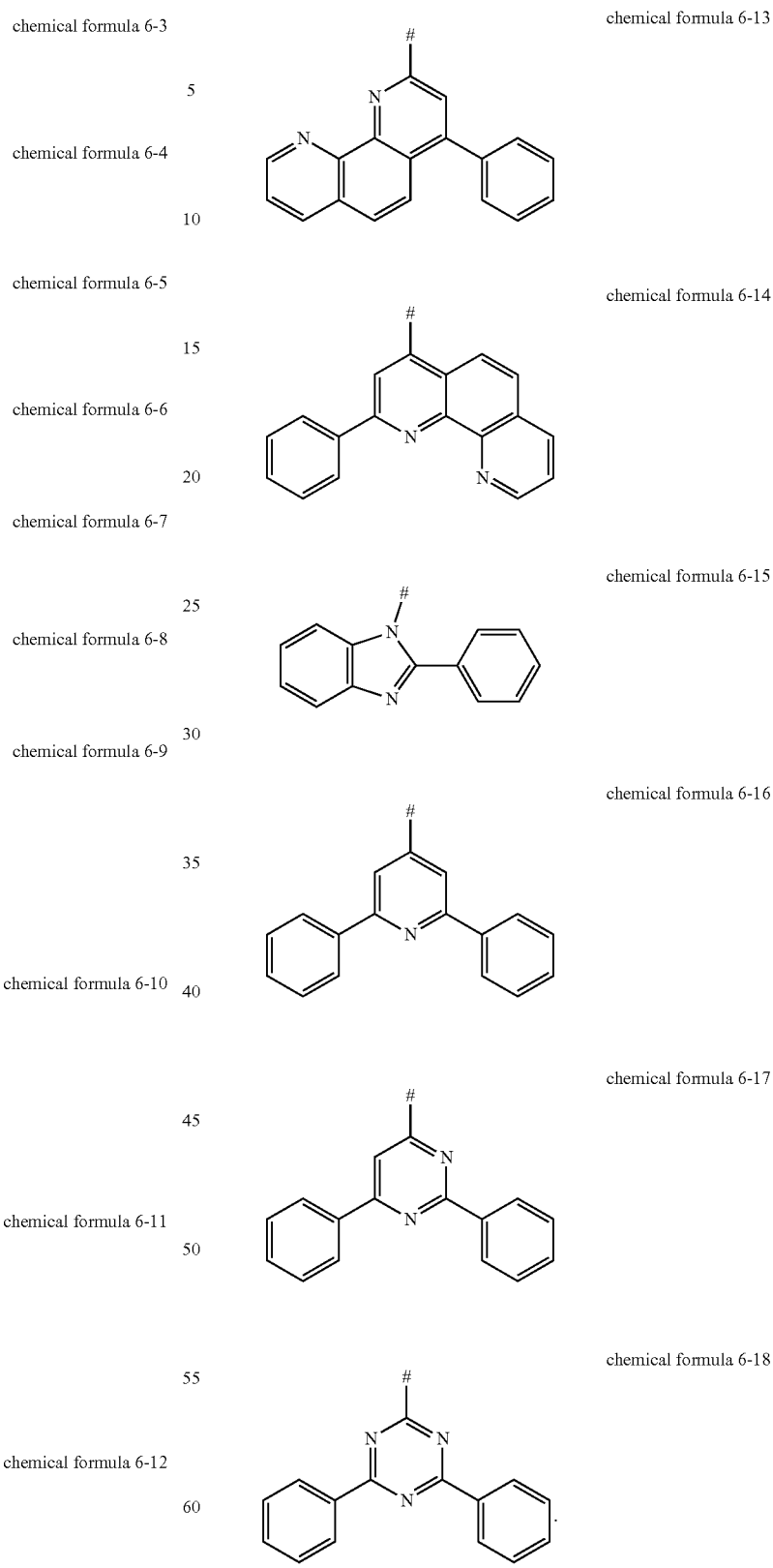
According to an embodiment of the compound of the present disclosure, the compound is selected from the group consisting of the following compounds:

E001
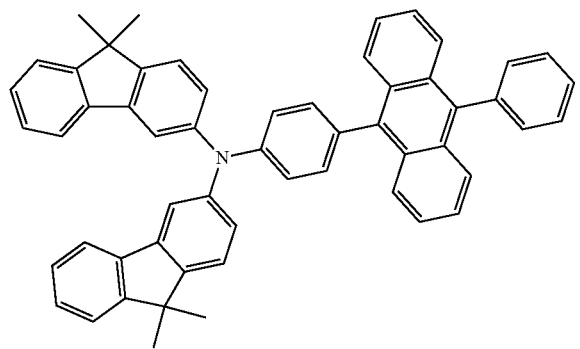
E005
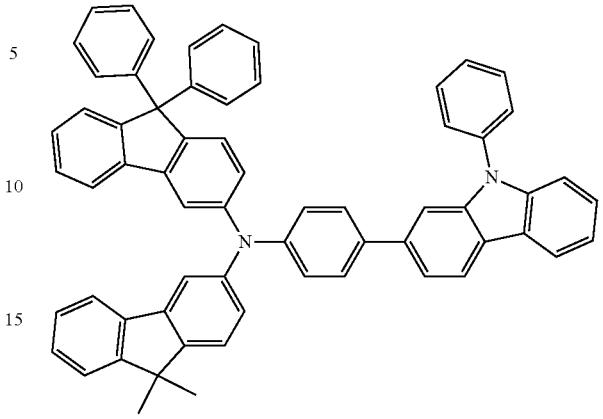
E002
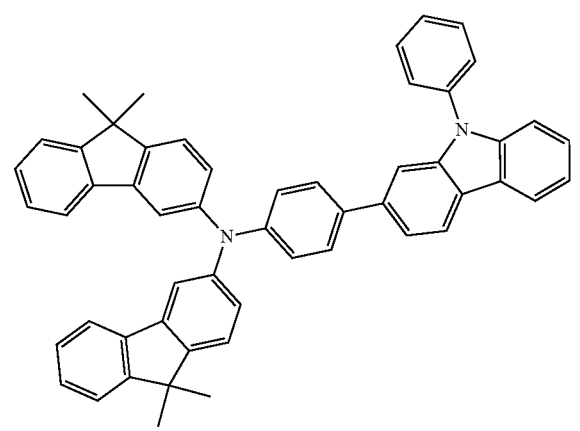
E006
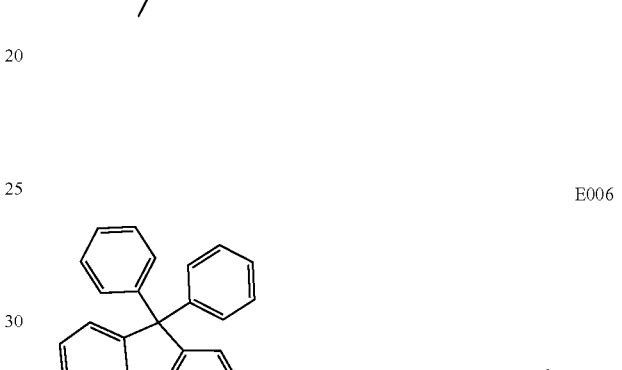
E003
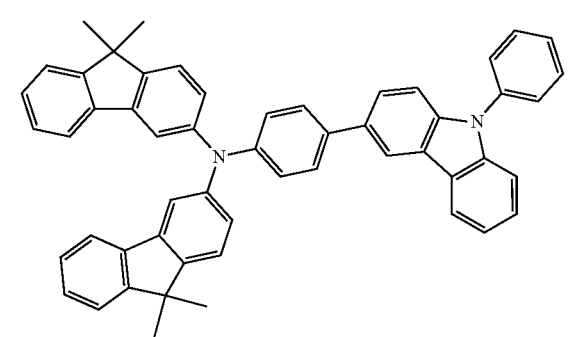
E004
E007
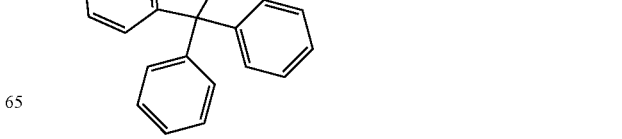

-continued
E008
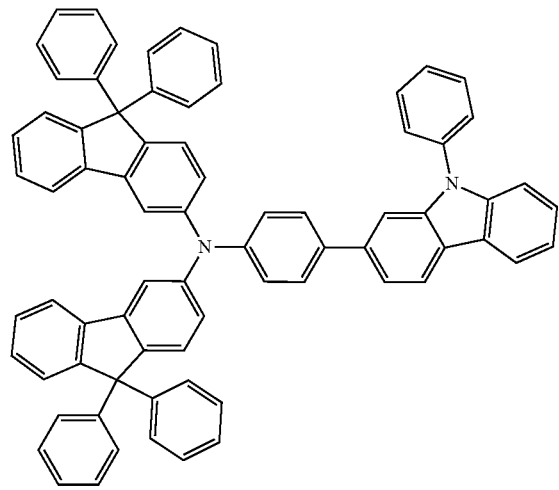
E009
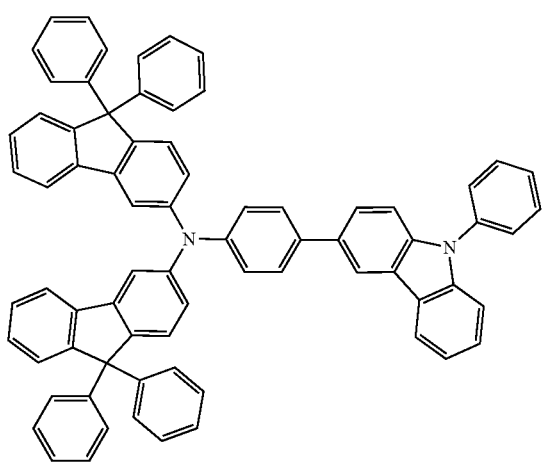
E010
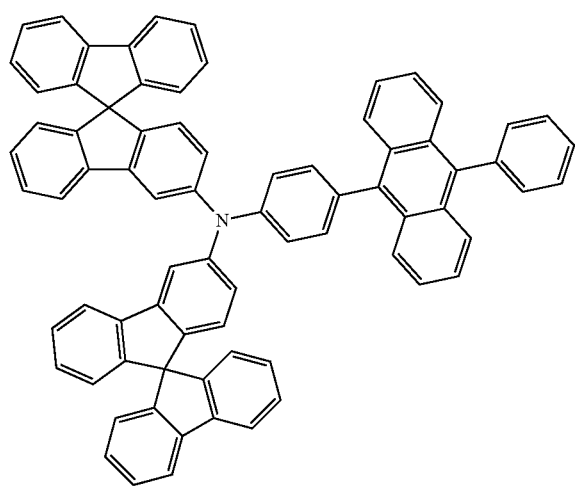
E011
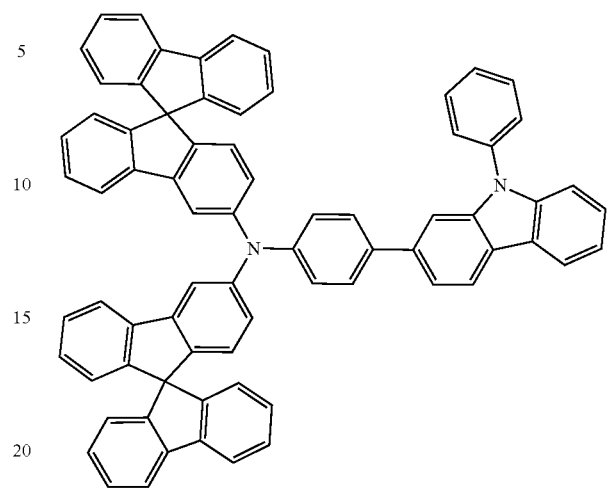
E012
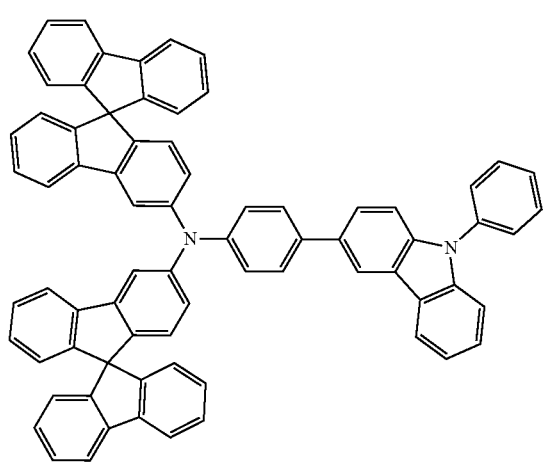
E013
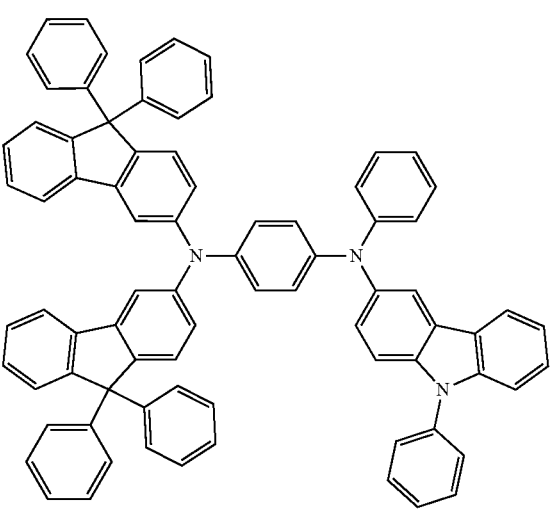

E014
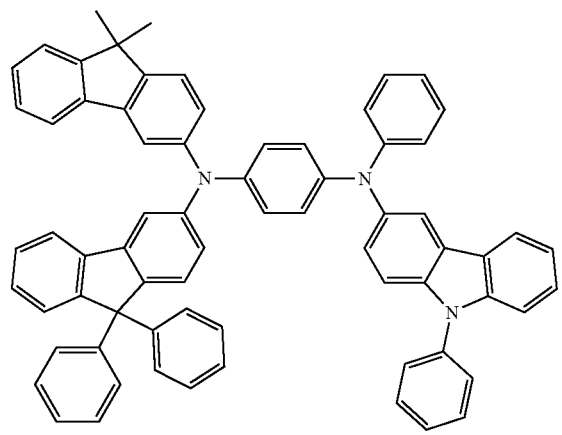
E015
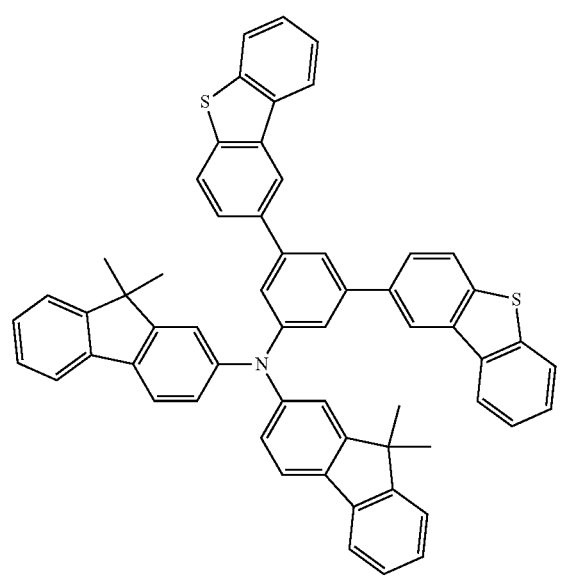
E016
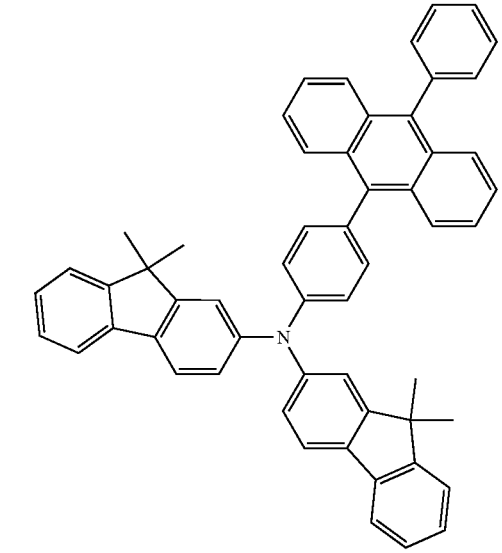
E017
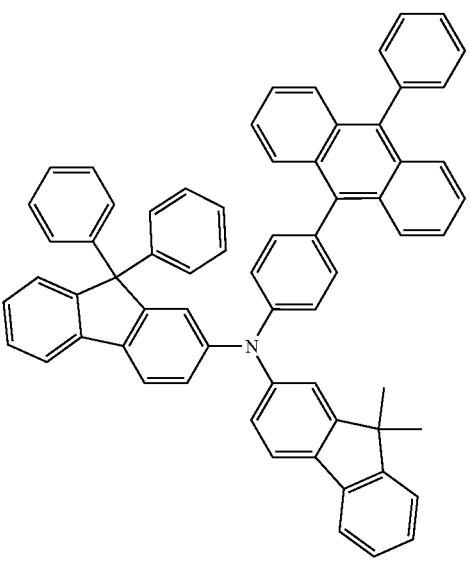
E018
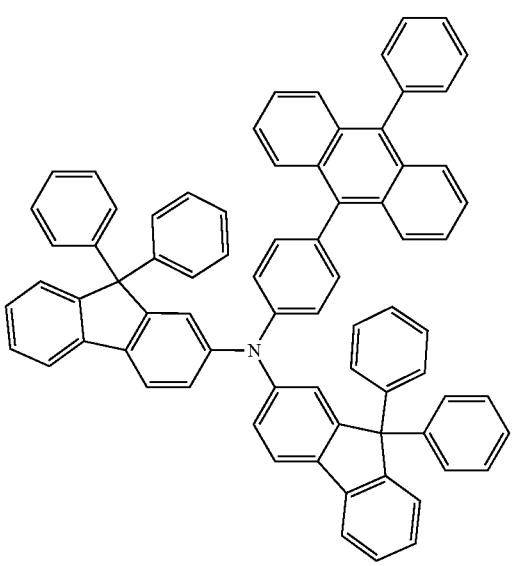

E019
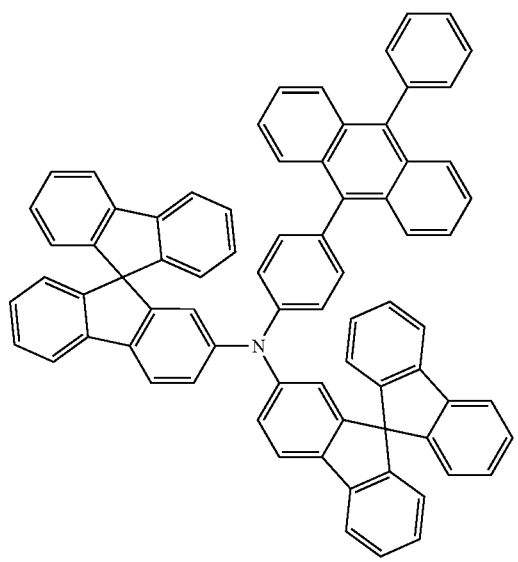
E021
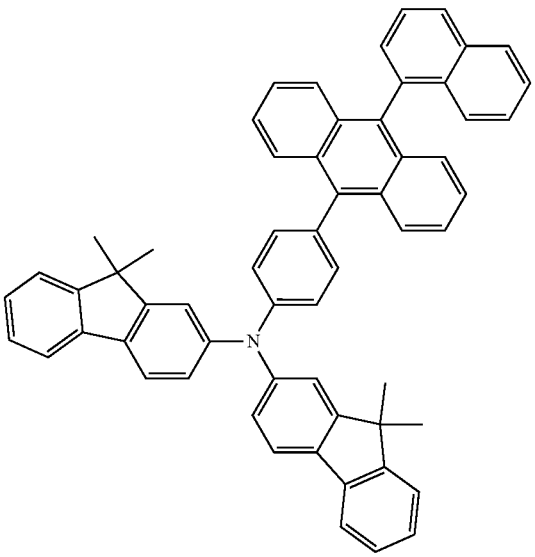
E020
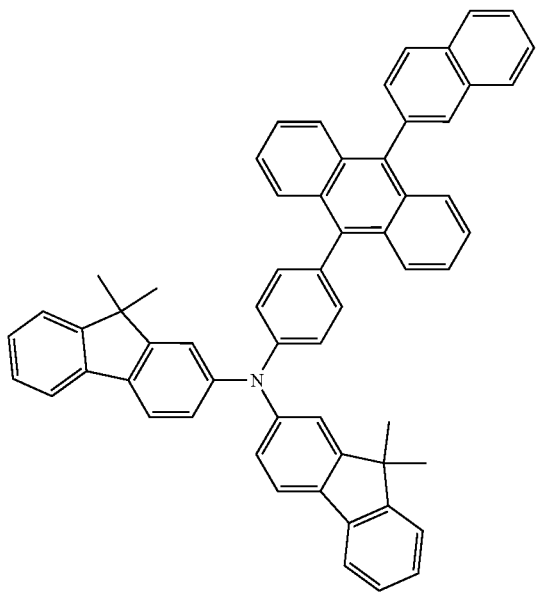
E022
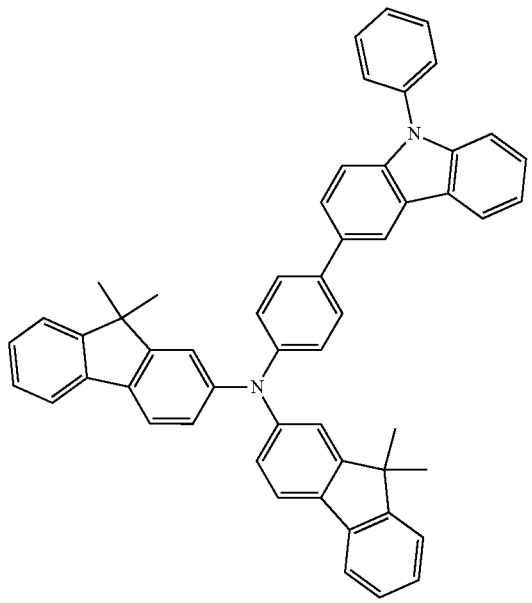

E023
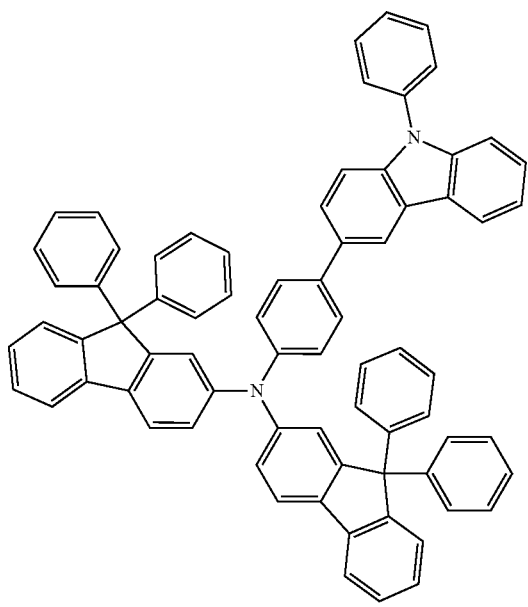
E025
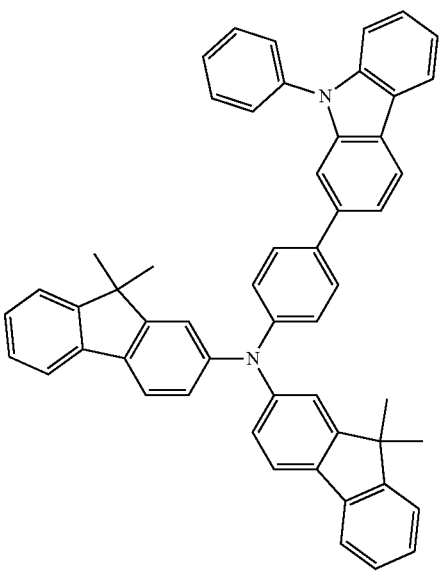
E024
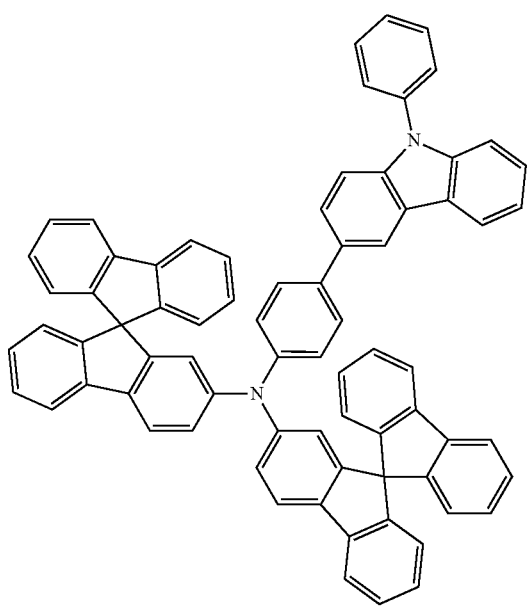
E026
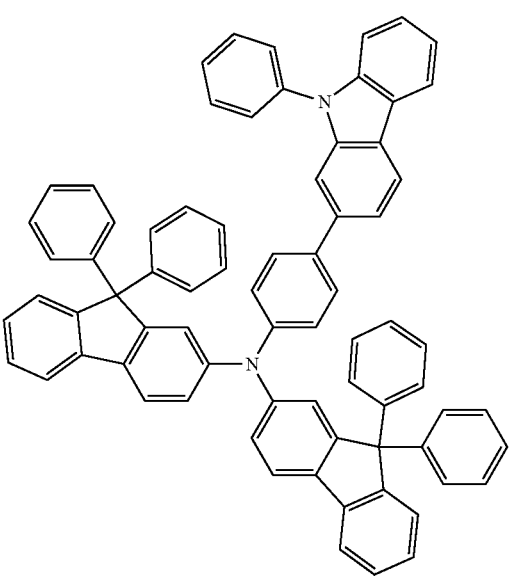

E027
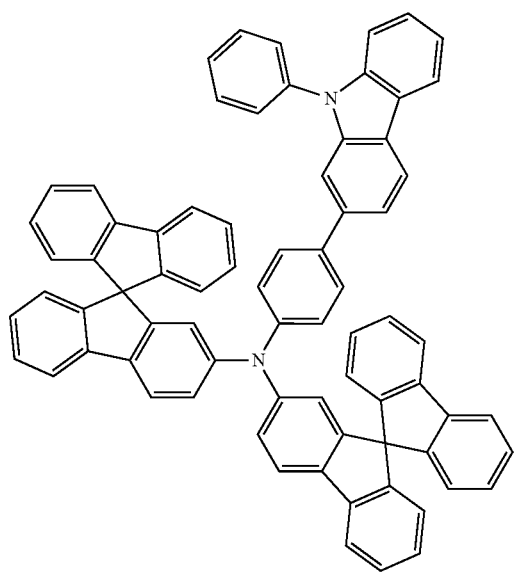
E028
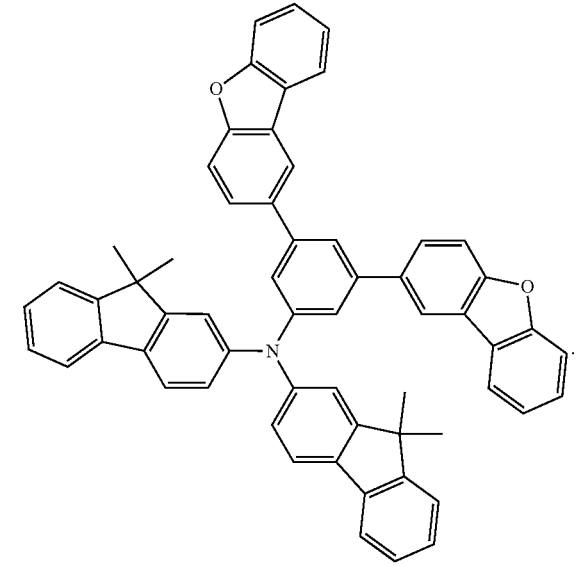
E030
According to an embodiment of the compound of the present disclosure, the compound is selected from the group consisting of the following compounds:
E031
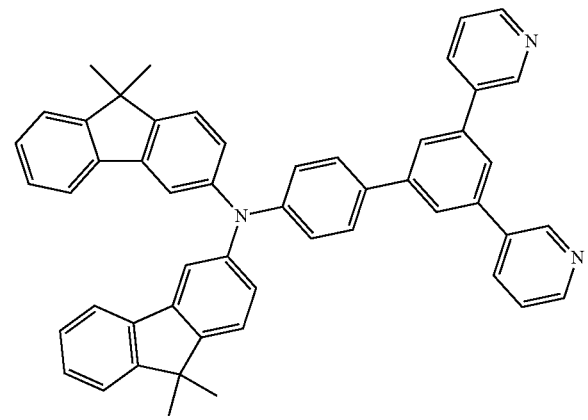
E032
E029
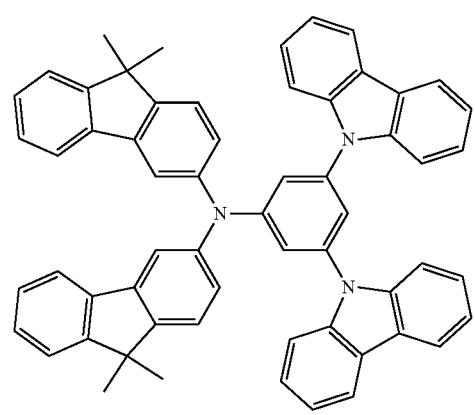

E033
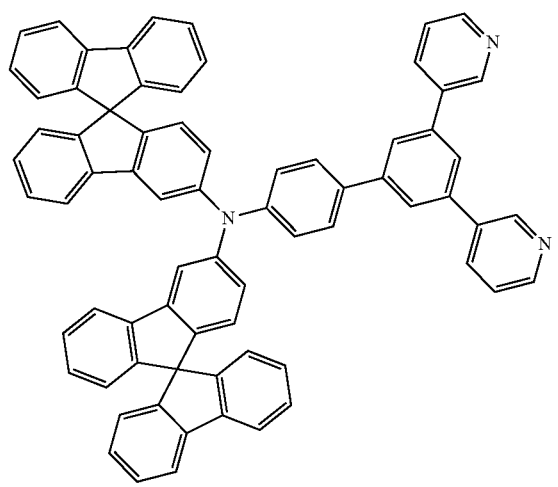
E036
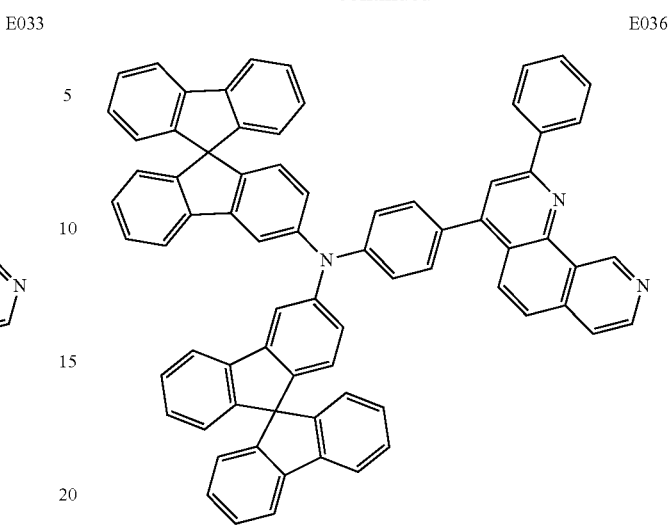
E034
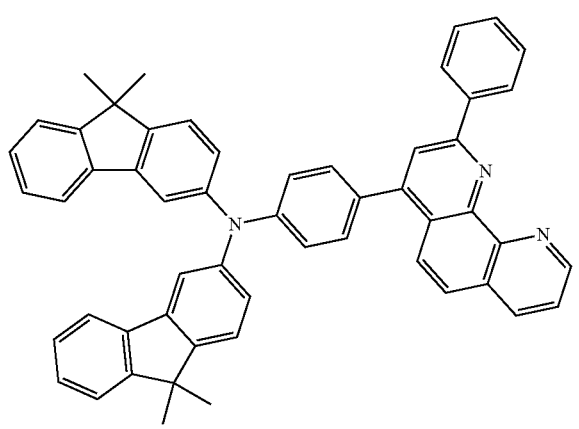
E037
E035
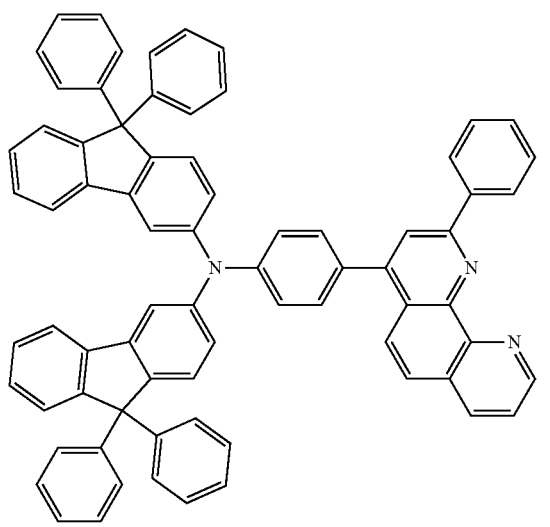
E038
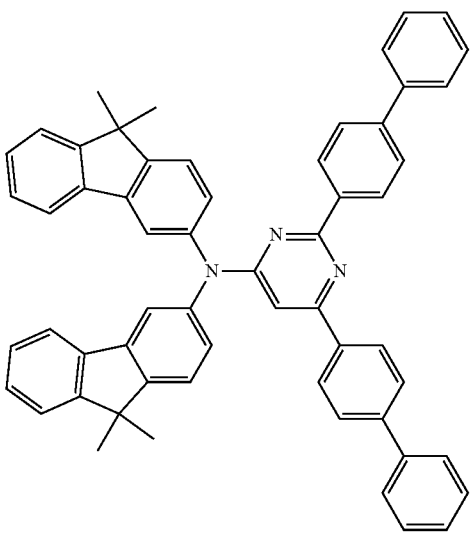

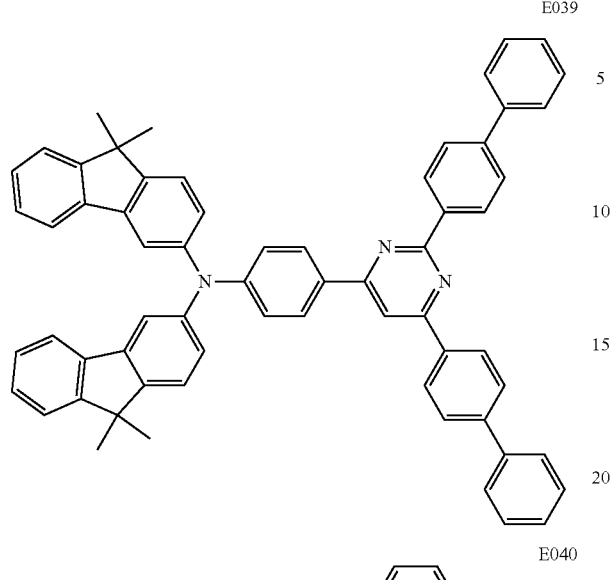
E039
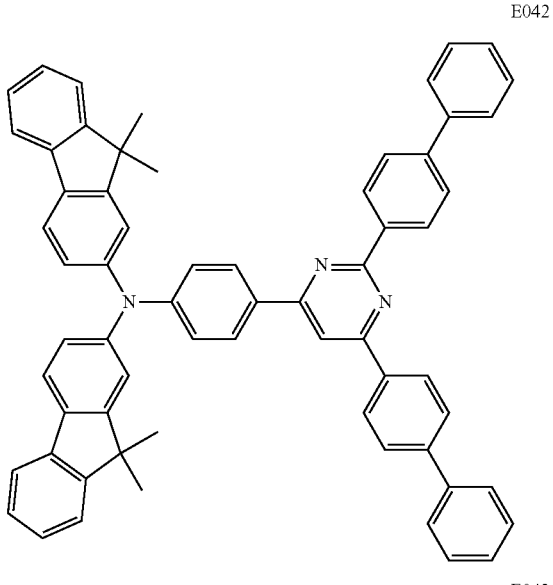
E042
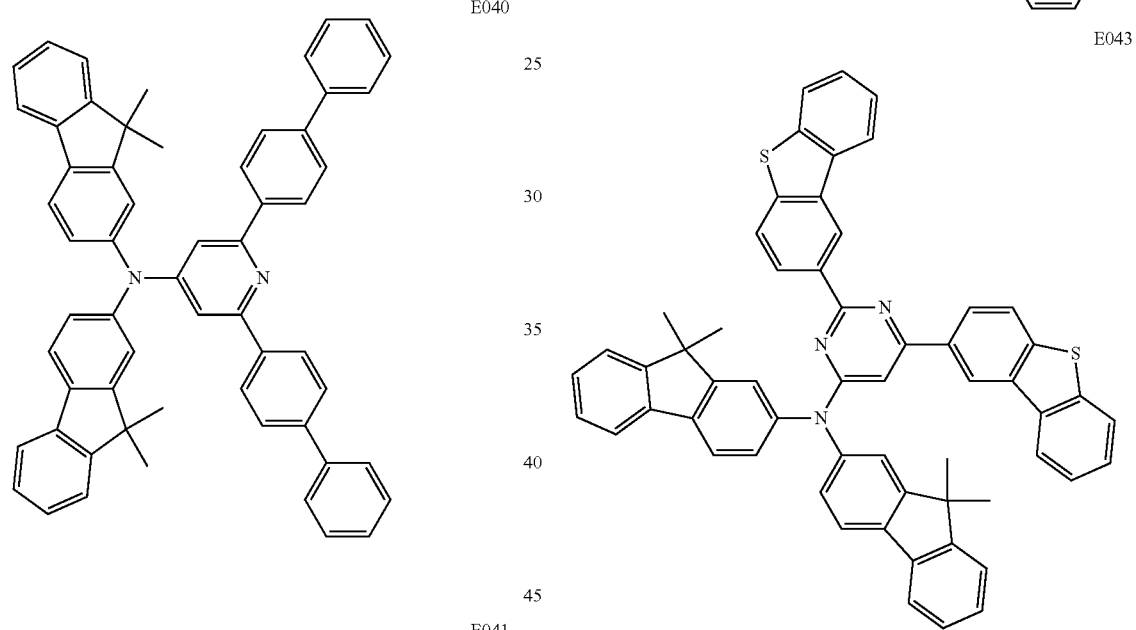
E040
E043
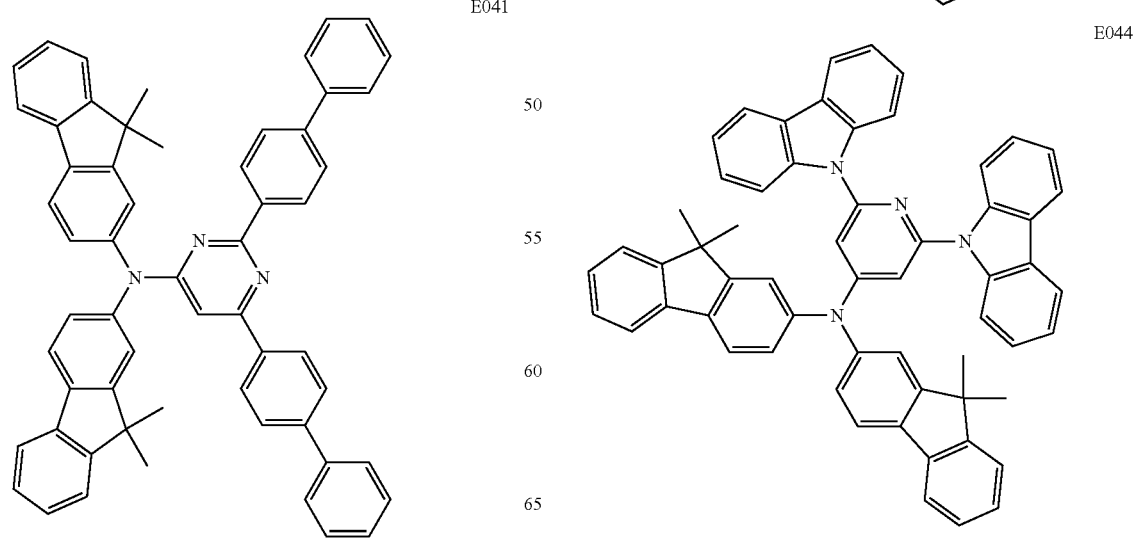
E041
E044

E045 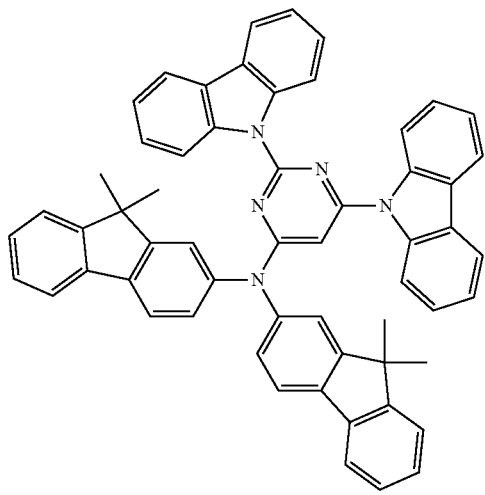

E046 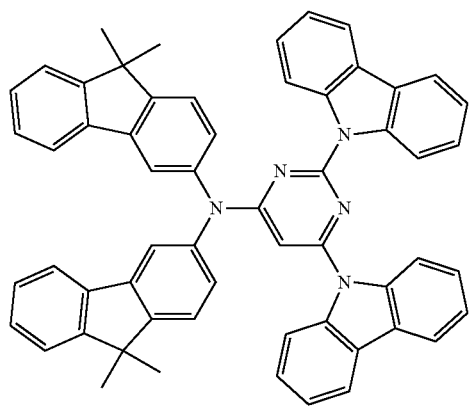

E047 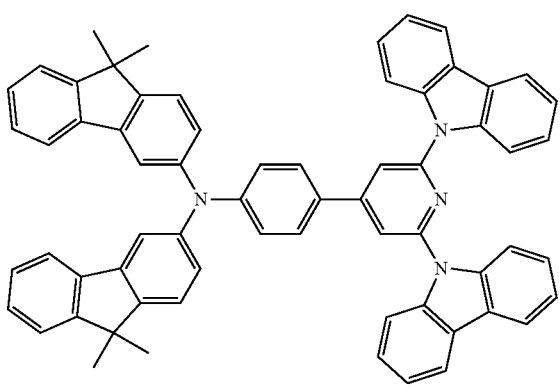

E048 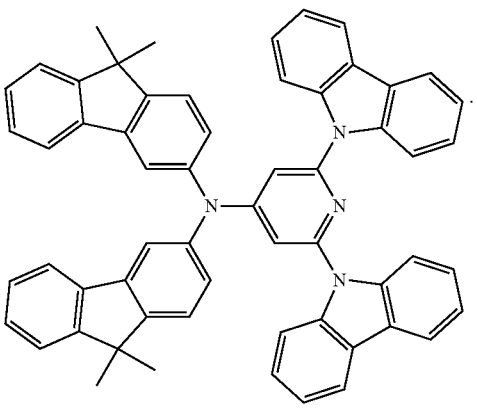

According to an embodiment of the compound of the present disclosure, a refractive index n of the compound for a visible light having a wavelength of 400 nm to 700 nm is greater than or equal to 1.9.

According to an embodiment of the compound of the present disclosure, an extinction coefficient k of the compound for a visible light having a wavelength of 430 nm to 700 nm is smaller than or equal to 0.0. The compound of the present disclosure contains an arylamine group, which interrupts conjugation to a certain extent. Therefore, the conjugate length of the compound is short, and the absorption is weakened, achieving a smaller extinction coefficient.

According to one embodiment of the present disclosure provides a display panel including an organic light-emitting device. The organic light-emitting device includes an anode, a cathode disposed oppositely to the anode, a capping layer disposed at a side of the cathode facing away from anode, and an organic layer disposed between the anode and the cathode. The organic layer includes an electron transmission layer, a hole transmission layer and a light-emitting layer, and the capping layer contains the compound according to one embodiment of the present disclosure.

According to an embodiment of the display panel of the present disclosure, a transmittance of the cathode together with the capping layer for a visible light of 400 to 700 nm is greater than 65%.

The present disclosure further provides a display panel including an organic light-emitting device, and the organic light-emitting device includes an anode, a cathode disposed oppositely to the anode, a capping layer disposed at a side of the cathode facing away from anode, and an organic layer disposed between the anode and the cathode. The organic layer includes an electron transmission layer, a hole transmission layer and a light-emitting layer disposed between the electron transmission layer and the hole transmission layer, and the electron transmission layer contains the compound according to one embodiment of the present disclosure.

According to an embodiment of the display panel of the present disclosure, an energy difference between a LUMO energy level of the compound and a LUMO energy level of a material of the light-emitting layer adjacent to the electron transmission layer is smaller than 0.2 eV; and a HOMO energy level of the compound is at least 0.3 eV greater than a HOMO energy level of the material of the light-emitting layer adjacent to the electron transmission layer.

According to an embodiment of the display panel of the present disclosure, the organic layer further comprises an electron injection layer adjacent to the electron transmission layer, an energy difference between a LUMO energy level of the compound and a LUMO energy level of a material of the electron injection layer is smaller than 0.2 eV, and a HOMO energy level of the compound is at least 0.3 eV greater than a HOMO energy level of the material of the electron transmission layer.

The present disclosure further provides a display panel including an organic light-emitting device, and the organic light-emitting device includes an anode, a cathode disposed oppositely to the anode, a capping layer disposed at a side of the cathode facing away from anode, and an organic layer disposed between the anode and the cathode. The organic layer includes an electron transmission layer, a hole transmission layer and a light-emitting layer disposed between the electron transmission layer and the hole transmission layer, and the hole transmission layer contains the compound according to the one embodiment of the present disclosure.

According to an embodiment of the above display panel of the present disclosure, an energy difference between a HOMO energy level of the compound and a HOMO energy level of a material of the light-emitting layer or hole transmission layer adjacent to the hole transmission layer is smaller than 0.2 eV; and a LUMO energy level of the compound is at least 0.3 eV greater than a LUMO energy level of the material of the light-emitting layer adjacent to the hole transmission layer.

Synthesis of the compound of the present disclosure is illustrated in the following examples. A general synthesis scheme of the compound of the present disclosure in chemical formula I is shown as follows:

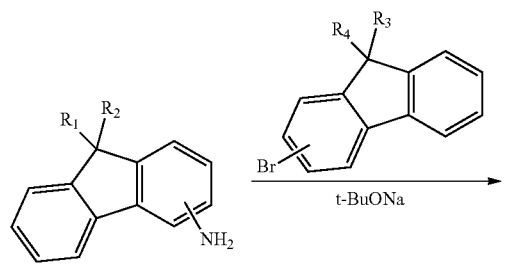

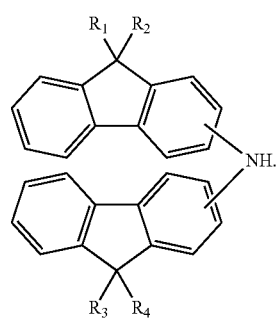

Example 1

Synthesis of Compound E003:

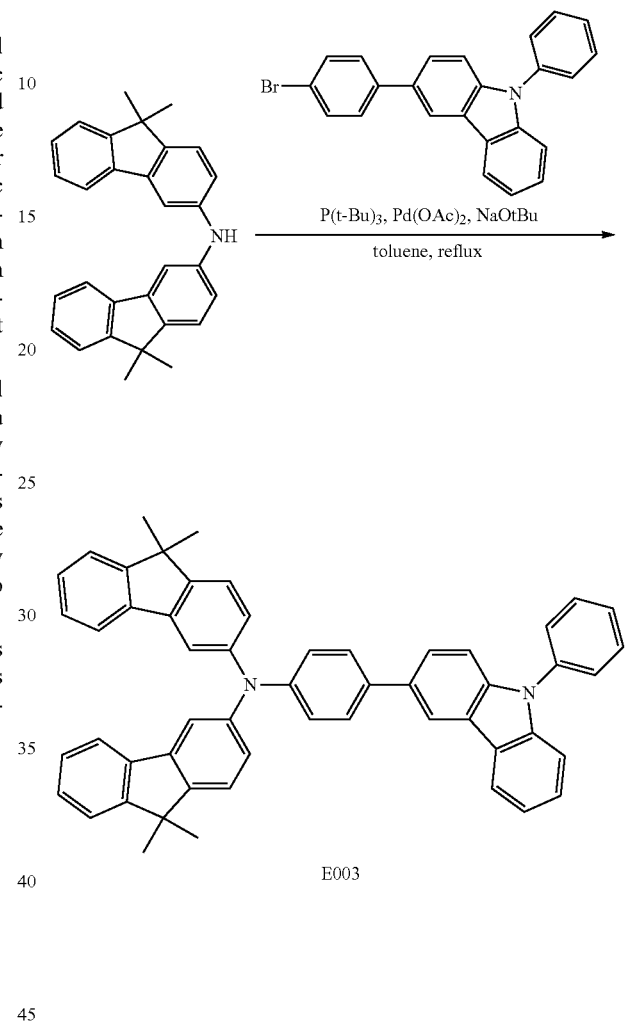

Tri-tert-butylphosphine (3 mL), palladium acetate (0.11 mmol) and sodium tert-butoxide (20 mmol) were added into a degassed toluene (500 mL) solution of 3-bromophenyl-9-phenylcarbazole (20 mmol) and di(dimethylfluorenyl)amine (20 mmol), and heated to reflux for 2 hours. The obtained reaction mixture was cooled to room temperature, diluted with toluene solvent and filtered through diatomite. The filtrate was diluted with water and extracted with toluene. The organic phase was collected and then deposited under vacuum. The residue was purified through a silica gel column and then recrystallized to obtain the target product E003.

Elementary analysis results of Compound E003 ($C_{54}H_{42}N_2$): theoretical value: C, 90.21; H, 5.89; N, 3.90; measured value: C, 90.20; H, 5.87; N, 3.91. ESI-MS(m/z) (M+) obtained by liquid chromatography-mass spectrometry: theoretical value: 718.33, measured value: 718.41.

Example 2

Synthesis of Compound E017:

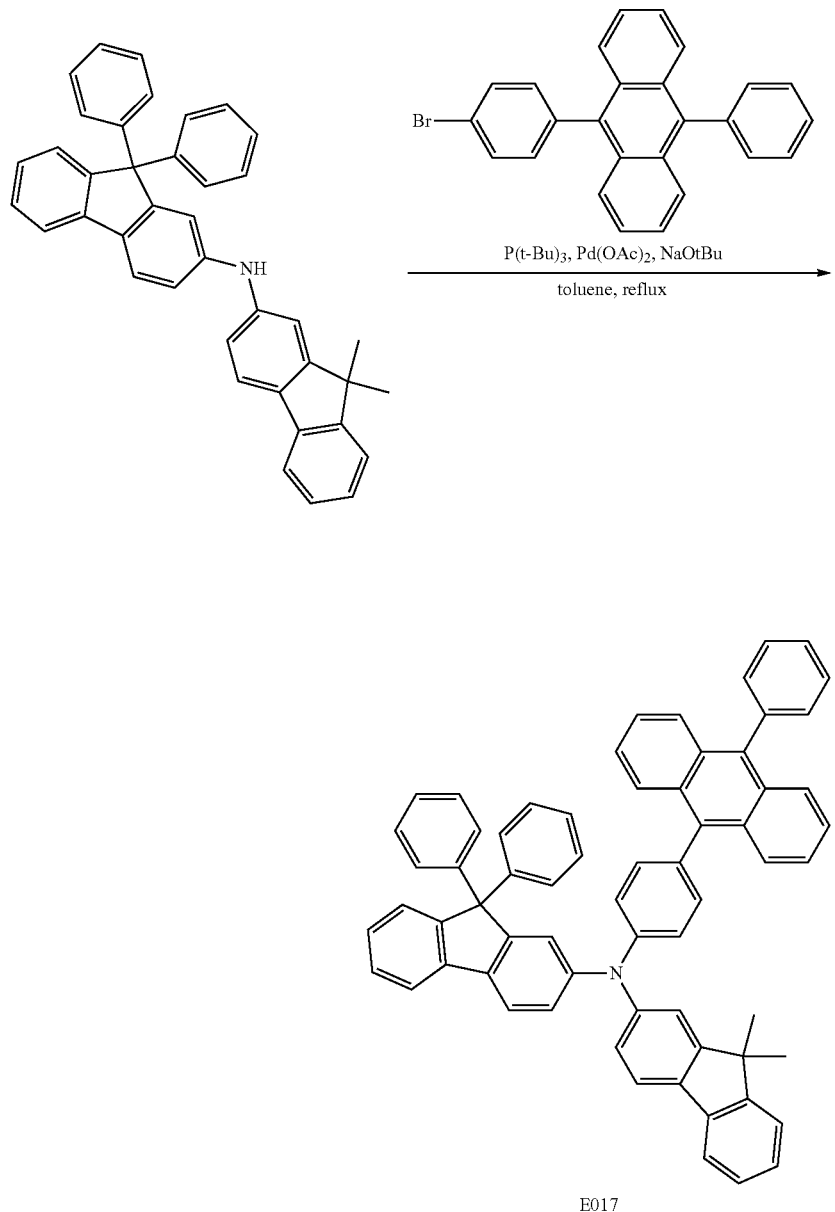

Tri-tert-butylphosphine (3 mL), palladium acetate (0.11 mmol) and sodium tert-butoxide (20 mmol) were added into a degassed toluene solution (500 mL) of 9-bromophenyl-10-phenylanthracene (20 mmol) and diphenylfluorenyl dimethylfluorenyl amine (20 mmol), and heated to reflux for 2 hours. The obtained reaction mixture was cooled to room temperature, diluted with toluene solvent and filtered through diatomite. The filtrate was diluted with water and extracted with toluene. The organic phase was collected and then deposited under vacuum. The residue was purified through a silica gel column and then recrystallized to obtain the target product E017.

Elementary analysis results of Compound E017 ($C_{66}H_{47}N$): theoretical value: C, 92.81; H, 5.55; N, 1.64; measured value: C, 92.80; H, 5.54; N, 1.66. ESI-MS(m/z) (M+) obtained by liquid chromatography-mass spectrometry: theoretical value: 853.37, measured value: 853.49.

Example 3

Synthesis of Compound E032:

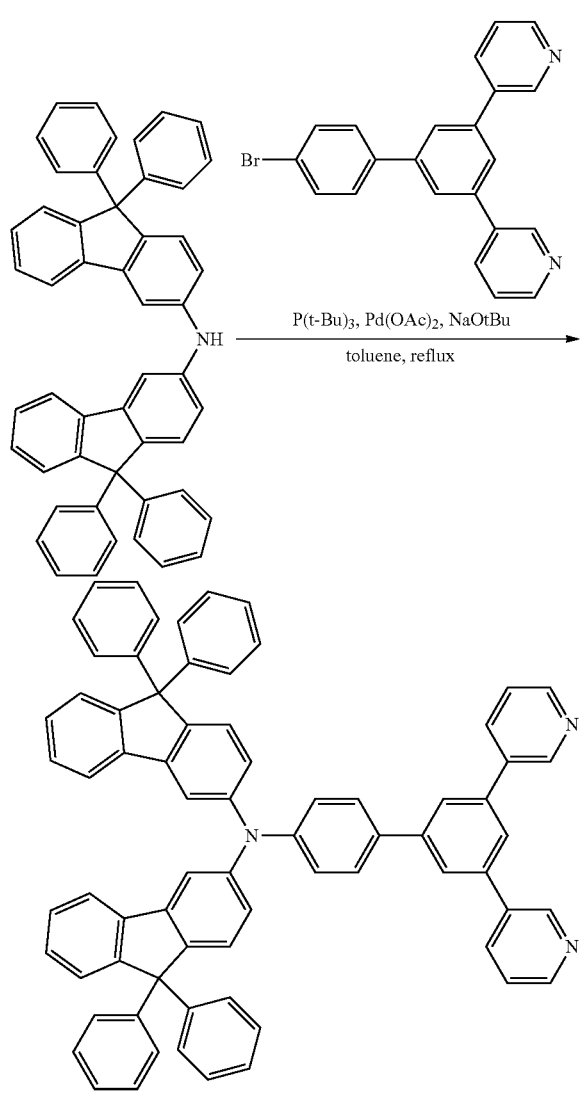

E032

Example 4

Synthesis of Compound E042:

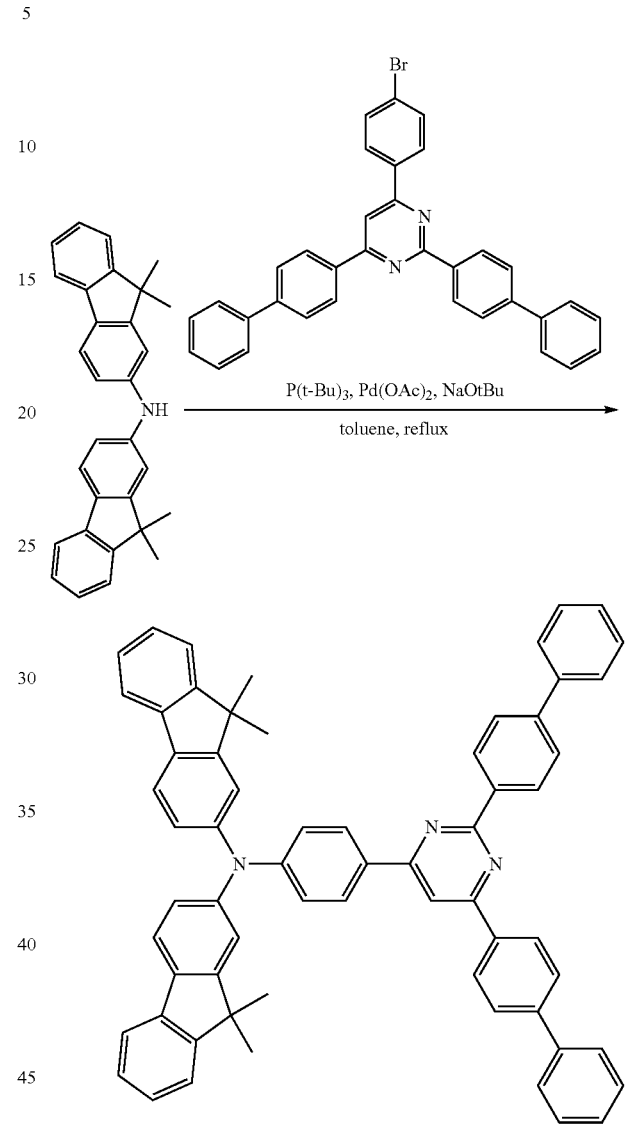

E042

Tri-tert-butylphosphine (3 mL), palladium acetate (0.11 mmol) and sodium tert-butoxide (20 mmol) were added into a degassed toluene solution (500 mL) of 3,5-dipyridyl-1-bromophenyl benzene (20 mmol) and di(diphenylfluorenyl) amine (20 mmol), and heated to reflux for 2 hours. The obtained reaction mixture was cooled to room temperature, diluted with toluene solvent and filtered through diatomite. The filtrate was diluted with water and extracted with toluene. The organic phase was collected and then deposited under vacuum. The residue was purified through a silica gel column and then recrystallized to obtain the target product E032.

Elementary analysis results of Compound E032 ($C_{72}H_{49}N_3$): theoretical value: C, 90.44; H, 5.17; N, 4.39; measured value: C, 90.44; H, 5.18; N, 4.38. ESI-MS(m/z) (M+) obtained by liquid chromatography-mass spectrometry: theoretical value: 955.39, measured value: 955.61.

Tri-tert-butylphosphine (3 mL), palladium acetate (0.11 mmol) and sodium tert-butoxide (20 mmol) were added into a degassed toluene (500 mL) solution of 2-biphenyl-4-biphenyl-6-bromophenyl pyrimidine (20 mmol) and di(dimethylfluorenyl) amine (20 mmol), and heated to reflux for 2 hours. The obtained reaction mixture was cooled to room temperature, diluted with toluene solvent and filtered through diatomite. The filtrate was diluted with water and extracted with toluene. The organic phase was collected and then deposited under vacuum. The residue was purified through a silica gel column and then recrystallized to obtain the target product E042.

Elementary analysis results of Compound E042 ($C_{64}H_{49}N_3$): theoretical value: C, 89.37; H, 5.74; N, 4.89; measured value: C, 89.37; H, 5.72; N, 4.91. ESI-MS(m/z) (M+) obtained by liquid chromatography-mass spectrometry: theoretical value: 859.39, measured value: 859.50.

Measurement results of energy levels and refractive indexes of the compounds of the examples of the present disclosure are listed in Table 1, and compared with those of comparative examples CBP, Alq3 and TPBI.

TABLE 1

Measurement results of energy levels and refractive indexes of compounds

| Compound | HOMO (eV) | LUMO (eV) | $E_T$ (eV) | Refractive index | | |
|---|---|---|---|---|---|---|
| | | | | n@450 | n@530 | n@620 |
| E003 | −5.723 | −2.467 | 2.736 | 2.14 | 2.06 | 1.96 |
| E017 | −5.748 | −2.586 | 1.853 | 2.15 | 1.99 | 1.92 |
| E032 | −5.686 | −2.631 | 2.809 | 2.08 | 1.95 | 1.90 |
| E042 | −5.775 | −2.628 | 2.784 | 2.11 | 1.97 | 1.91 |
| CBP | −5.618 | −2.331 | 2.961 | 1.87 | 1.81 | 1.78 |
| Alq3 | −5.658 | −2.739 | 2.116 | 1.78 | 1.75 | 1.73 |
| TPBi | −5.968 | −2.354 | 2.832 | 1.80 | 1.76 | 1.73 |

*Take n@450 as an example, n@450 indicates a refractive index of the compound for light having a wavelength of 450 nm.

It can be seen from the Table 1 that the refractive index of each of the compounds E003, E017, E032 and E042 according to the present disclosure is greater than 1.9 for a visible light having a wavelength of 450 to 620 nm, conforming to the refractive index requirement on the capping layer (CPL) material of the light-emitting device. Compared with the conventional compounds CBP, Alq3 or TPBi, the compounds according to the present disclosure used as the CPL material has a higher refractive index. Furthermore, the compounds E003, E017, E032 and E042 according to the present disclosure have deeper HOMO levels and can effectively restrict holes inside the light-emitting layer. Besides, the compounds E003, E017 and E032 have a relatively higher triplet energy level (>2.75 eV) (the molecule of the Compound E017 contains a special group, and the charge transmission mechanism thereof is different, so that a triplet energy level of 1.853 eV is also sufficient for effective transmission), thereby effectively avoiding an inverse transmission of electric charge and achieving a higher luminous efficiency.

Example 5

Figure 2:
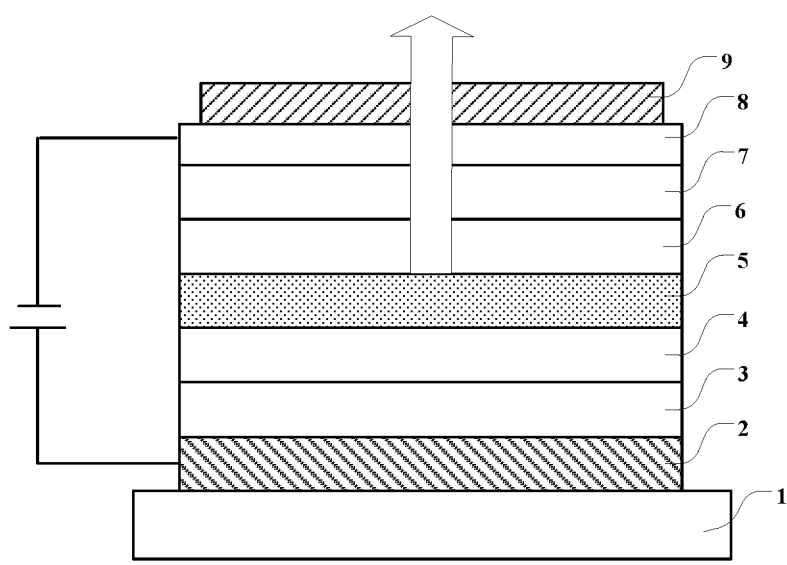
FIG. 2 is a schematic structural diagram of an OLED device according to an embodiment of the present disclosure.

This example provides an organic light-emitting device. As shown in FIG. 2, the organic light-emitting device includes a glass substrate 1, an ITO anode 2, a first hole transmission layer 3, a second hole transmission layer 4, a light-emitting layer 5, a first electron transmission layer 6, a second electron transmission layer 7, a cathode 8 (magnesium-silver electrode with a mass ratio of magnesium to silver of 9:1) and a capping layer (CPL) 9. The ITO anode 2 has a thickness of 15 nm, the first hole transmission layer 3 has a thickness of 10 nm, a second hole transmission layer 4 has a thickness of 95 nm, the light-emitting layer 5 has a thickness of 30 nm, the first electron transmission layer 6 has a thickness of 35 nm, the second electron transmission layer 7 has a thickness of 5 nm, the magnesium-silver electrode 8 has a thickness of 15 nm, and the capping layer (CPL) 9 has a thickness of 100 nm.

The organic light-emitting device according to the present disclosure is prepared according to the following steps:

1) the glass substrate 1 is cut into a size of 50mm×50mm× 0.7mm, then subjected to ultrasonic treatment respectively in isopropanol and deionized water for 30 minutes, and then exposed to ozone for cleaning for about 10 minutes, and then the obtained glass substrate 1 having the ITO anode 2 is installed onto a vacuum deposition device;

2) a hole transmission layer material HAT-CN is vacuum deposited onto the ITO anode 2 to form the first hole transmission layer 3 having a thickness of 10 nm;

3) a material TAPC is vacuum deposited onto the first hole transmission layer 3 to form the second hole transmission layer 4 having a thickness of 95 nm;

4) DPVBi as a host material and BCzVBi as a doping material are co-deposited on the hole transmission layer 4 with a mass ratio of DPVBi to BCzVBi is 1:19 to form the light-emitting layer 5 having a thickness of 30 nm;

5) a material BPhen is vacuum deposited on the light-emitting layer 5 to form the first electron transmission layer 6 having a thickness of 35 nm;

6) a material Alq3 is vacuum deposited on the first electron transmission layer 6 to form the second electron transmission layer 7 having a thickness of 5 nm;

7) the magnesium silver electrode having a thickness of 15 nm is vacuum deposited on the second electron transmission layer 7 as the cathode 8, in which a mass ratio of Mg to Ag is 9:1; and 8) the Compound E003 of the present disclosure is vacuum deposited on the cathode 8 to form the capping layer (CPL) having a thickness of 100 nm.

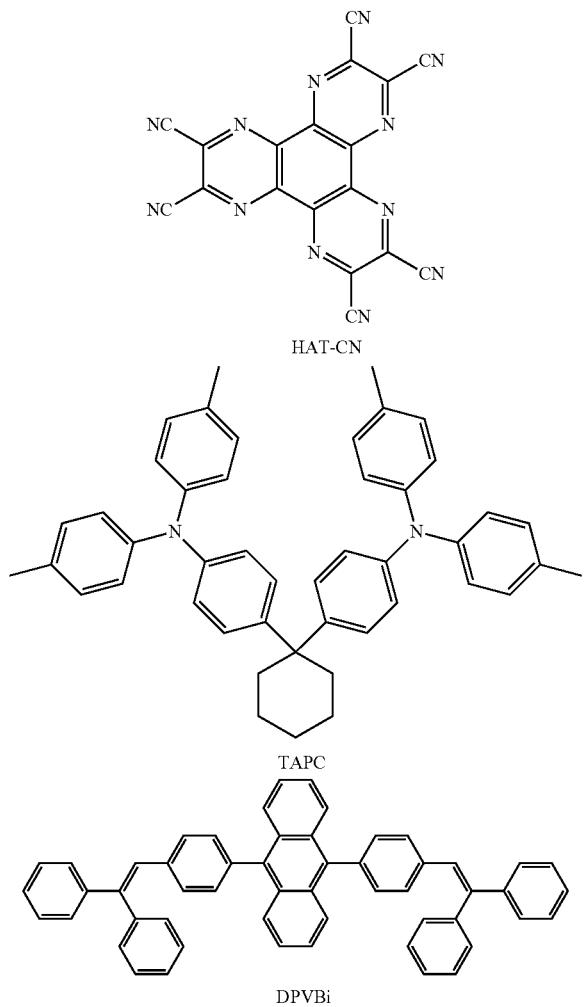

-continued

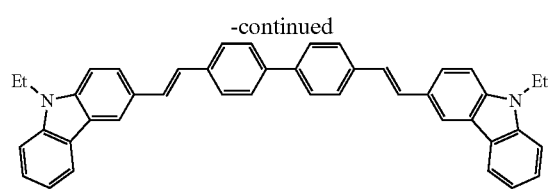
BCzVBi

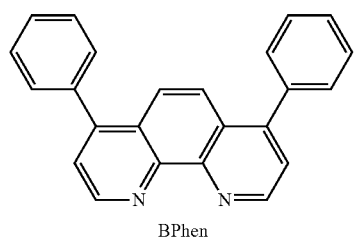
BPhen

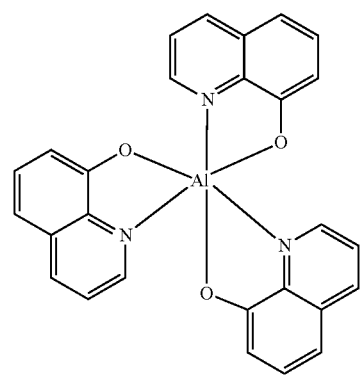
Alq3

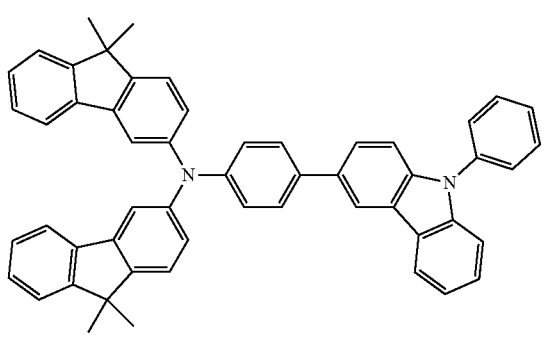
E003

Example 6

The organic light-emitting device of Example 5 is prepared according to the same steps as described in Example 5, except that the capping layer is made of Compound E017, and the other layers are the same as those in Example 5.

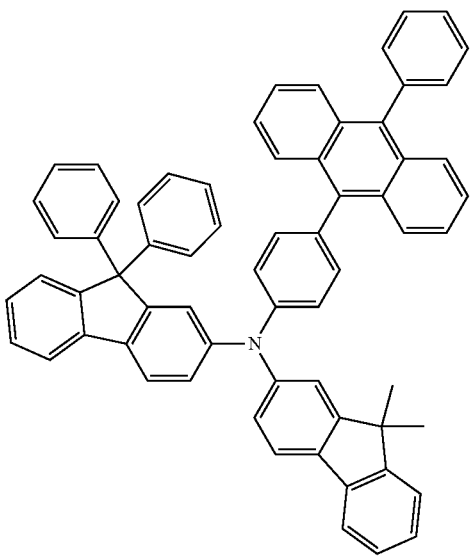
E017

Example 7

The organic light-emitting device of Example 7 is prepared according to the same steps as described in Example 5, except that the capping layer is made of Compound E032, and the other layers are the same as those in Example 5.

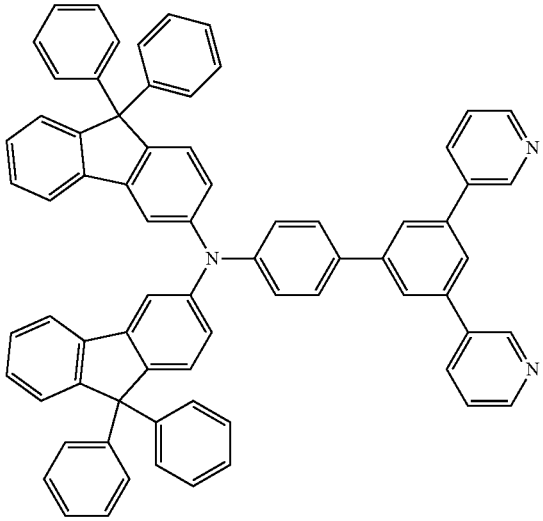
E032

Example 8

The organic light-emitting device of Example 8 is prepared according to the same steps as described in Example 5, except that the capping layer is made of Compound E042, and the other layers are the same as those in Example 5.

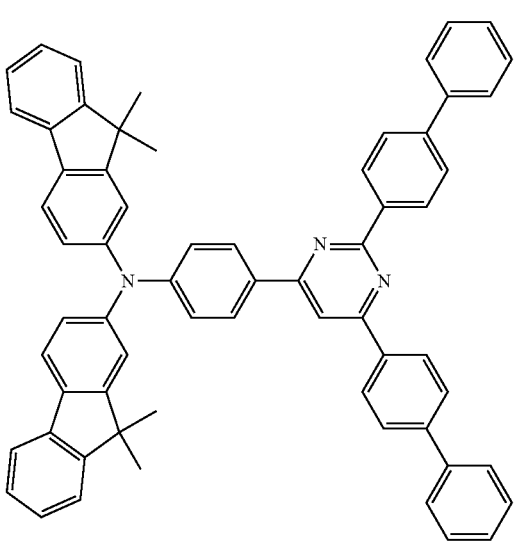

Comparative Example 1'

The organic light-emitting device of Comparative Example 1' is prepared according to the same steps as described in Example 5, except that the capping layer is made of CBP, and the other layers are the same as those in Example 5.

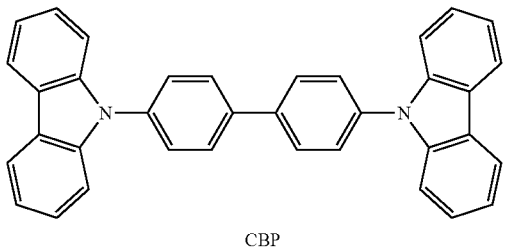 [SMILES: c1ccc2c(c1)c1ccccc1n2-c1ccc(-c2ccc(-n3c4ccccc4c4ccccc43)cc2)cc1 ; "CBP"]

CBP

Table 2

Test results of luminous performance of devices

| NO. | CPL material | Driving voltage (V) | EQE/% | E/CIEy |
|---|---|---|---|---|
| Example 5 | E003 | 3.77 | 5.57% | 75.6 |
| Example 6 | E017 | 3.80 | 5.25% | 78.1 |
| Example 7 | E032 | 3.86 | 5.63% | 77.9 |
| Example 8 | E042 | 3.84 | 5.08% | 75.4 |
| Comparative Example 1' | CBP | 4.10 | 4.29% | 63.7 |

It can be seen from the Table 2 that the driving voltages of the light-emitting devices that use the compounds according to the present disclosure as the CPL material are about 8% lower than that of the light-emitting device of Comparative Example 1', so that the power consumption of the light-emitting devices can be effectively reduced. Compared with the device of Comparative Example 1', both the external quantum efficiency (EQE) and the current efficiency of the light-emitting devices that use the compounds according to the present disclosure as the CPL material are significantly increased by about 18% and 20%, respectively. The compounds according to the present disclosure can have the similar effects when used as the material of the electron transmission layer.

The embodiments of the present disclosure further provide a display panel including the light-emitting device as described above.

Figure 3:
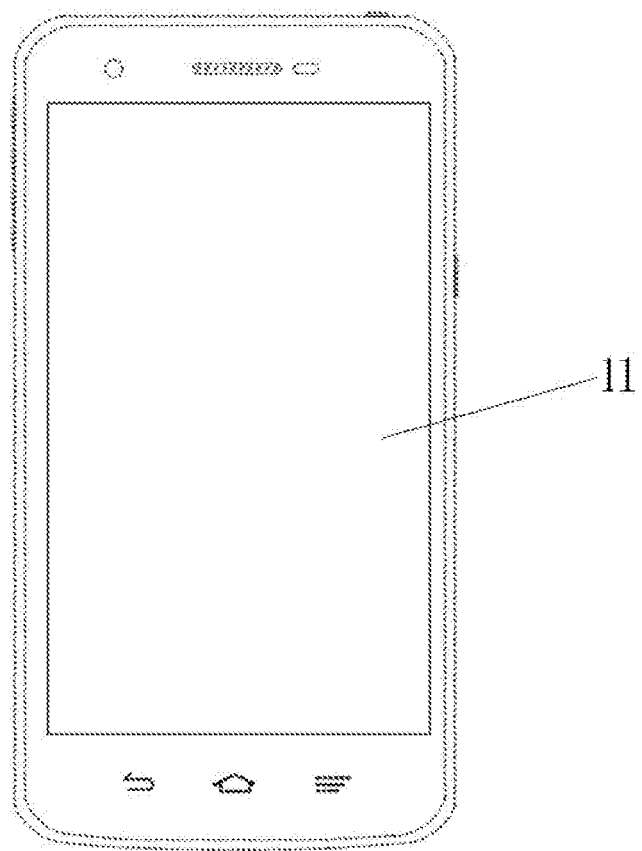
FIG. 3 is a schematic diagram of a display apparatus according to an embodiment of the present disclosure.

In the present disclosure, the organic light-emitting device can be an OLED applicable in an organic light-emitting display apparatus. The organic light-emitting display apparatus can be a mobile phone display screen, a computer display screen, a liquid crystal television display screen, a smart watch display screen, a smart automobile display panel, a VR or AR helmet display screen, or a display screen of other kinds of smart apparatus. FIG. 3 is a schematic diagram of a display apparatus according to an embodiment of the present disclosure. In FIG. 3, reference sign 11 indicates a mobile phone display screen.

What is claimed is:

1. A compound being selected from the group consisting of the following compounds:

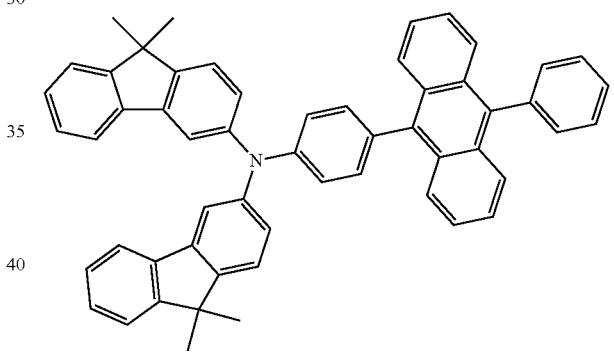

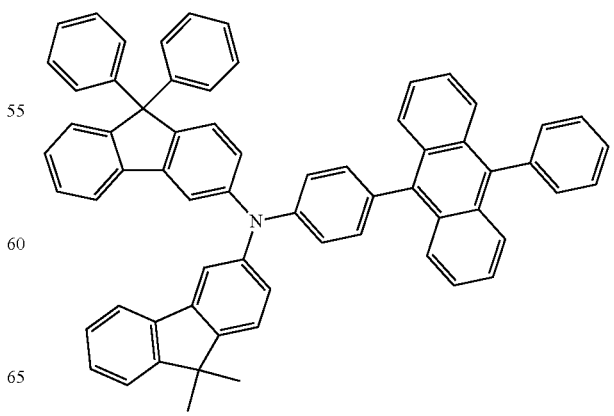

E007
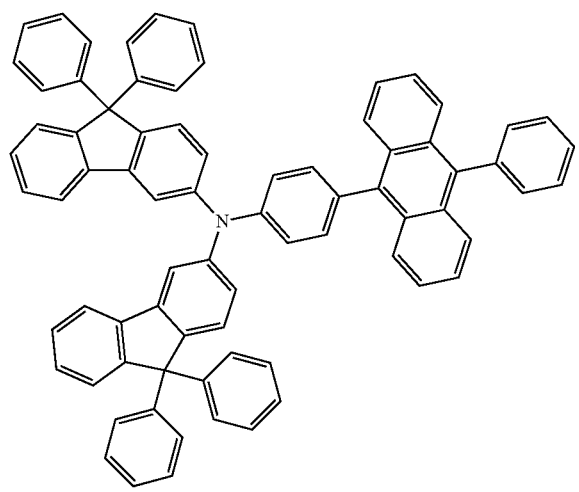
E010
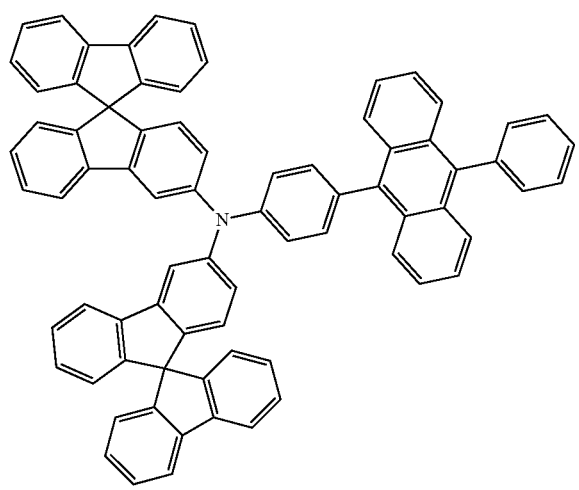
E013
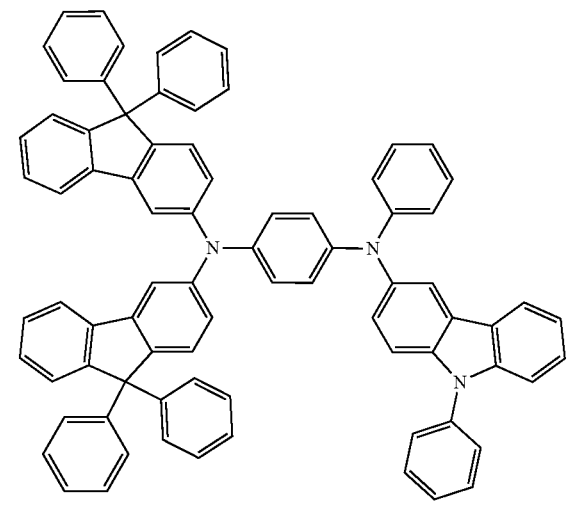
E014
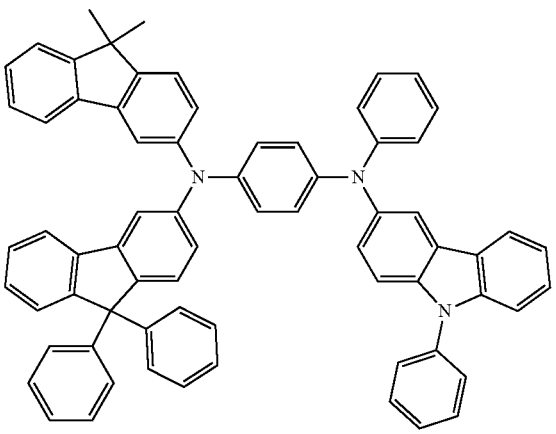
E015
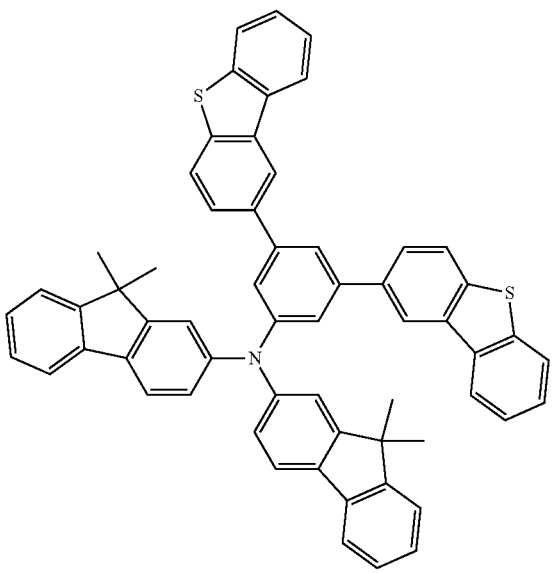
E016
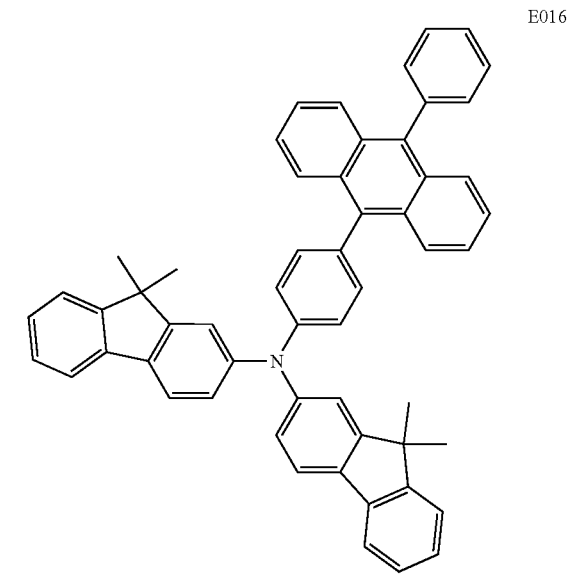

E017
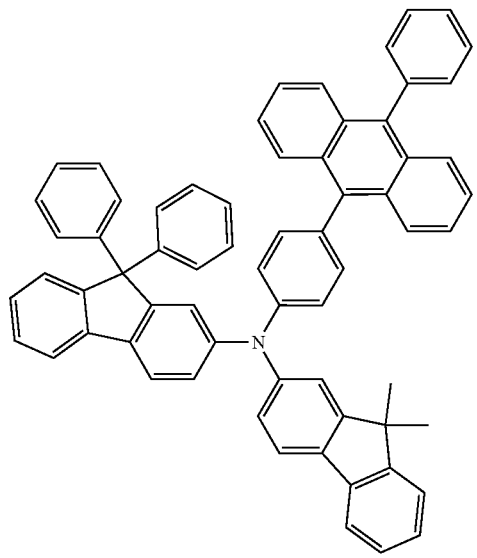
E018
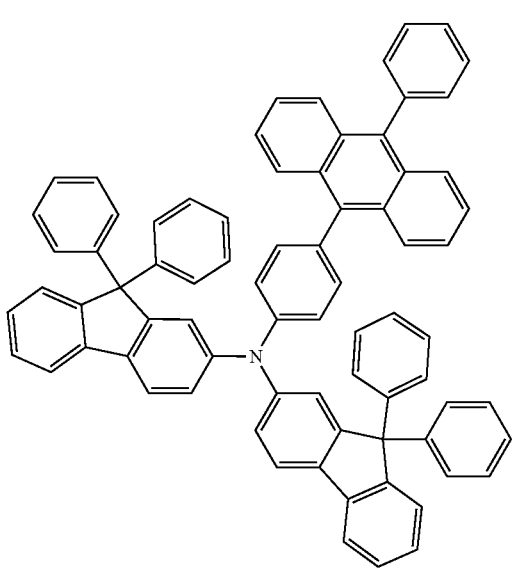
E019
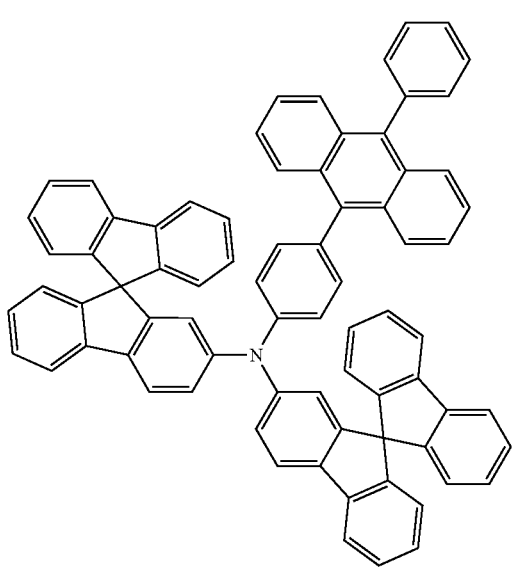
E020
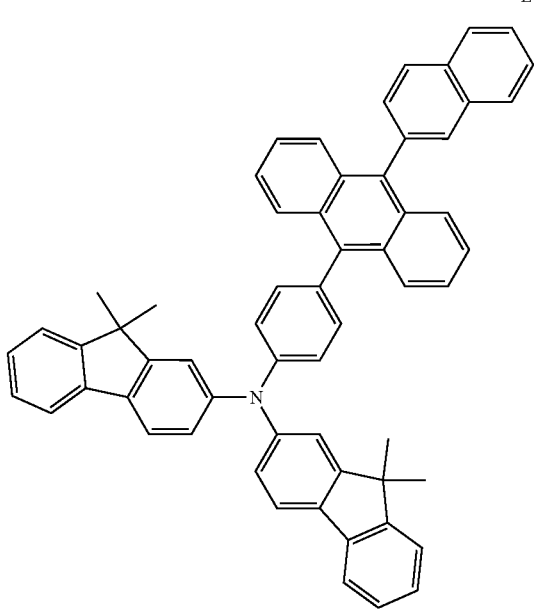

-continued
E021
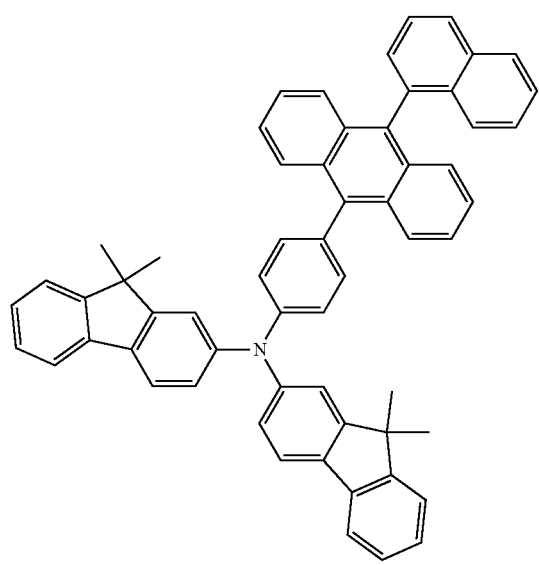
E029
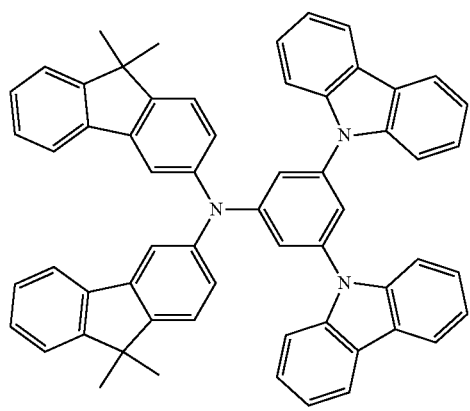
E030
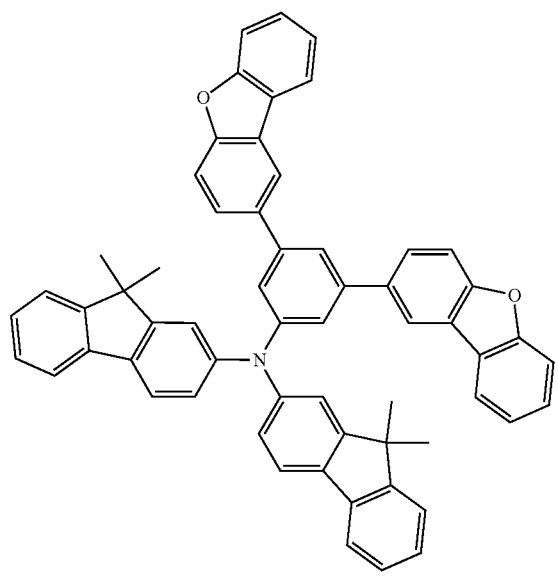
E031
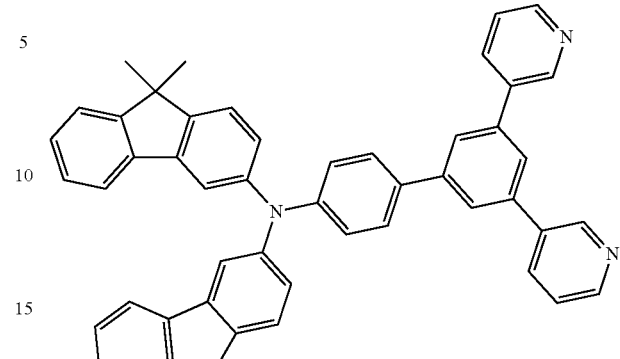
E032
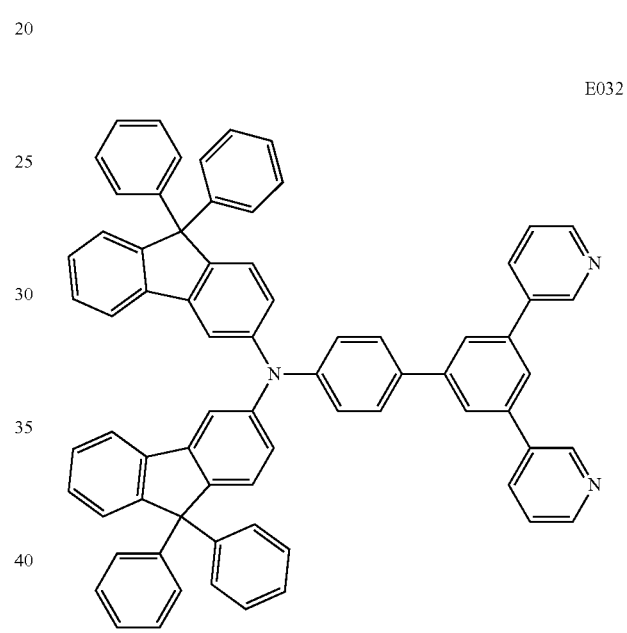
E033
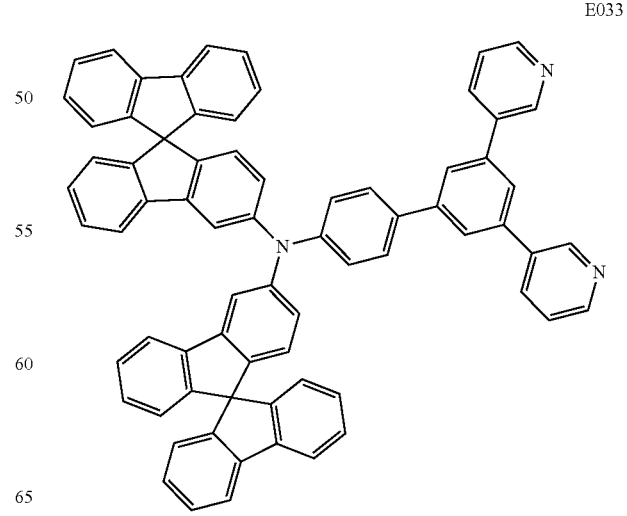

E034
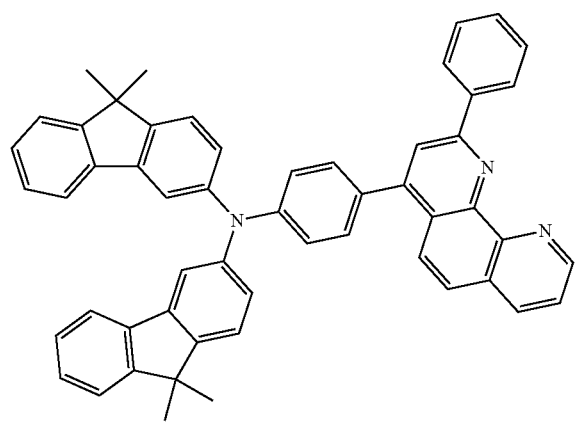
E035
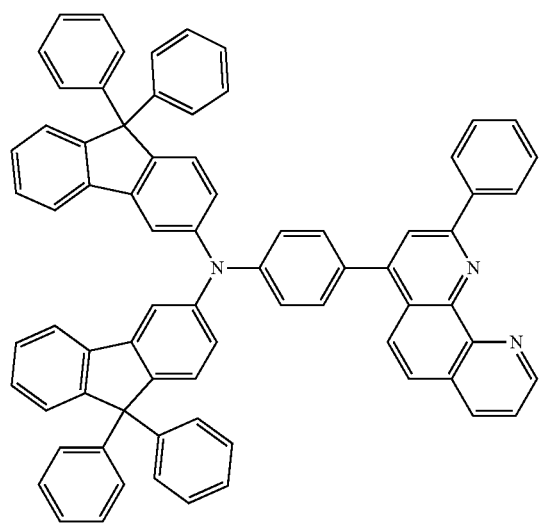
E036
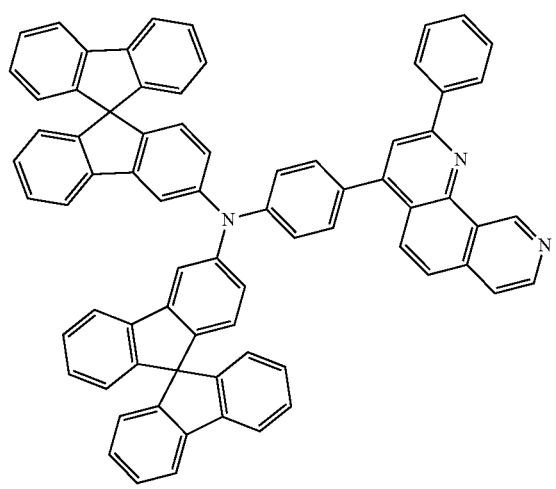
E037
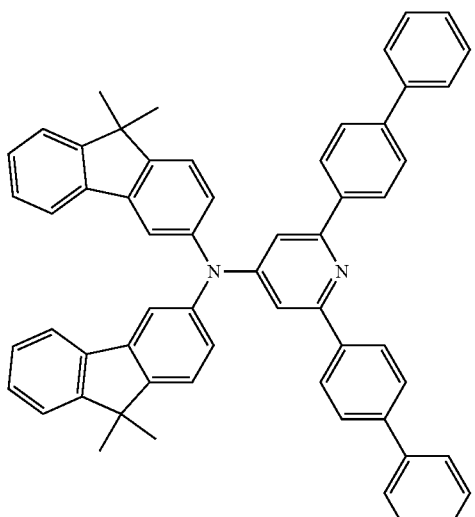
E038
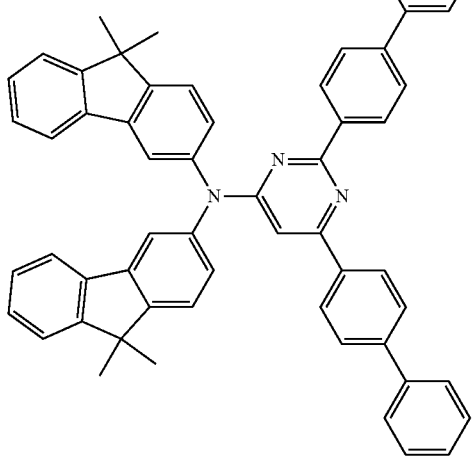
E039
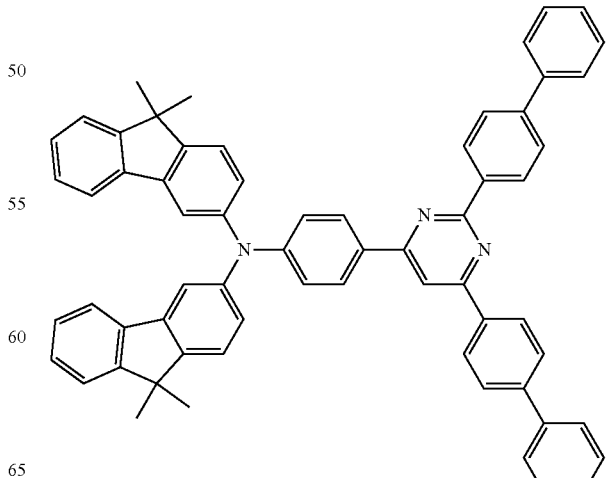

E040
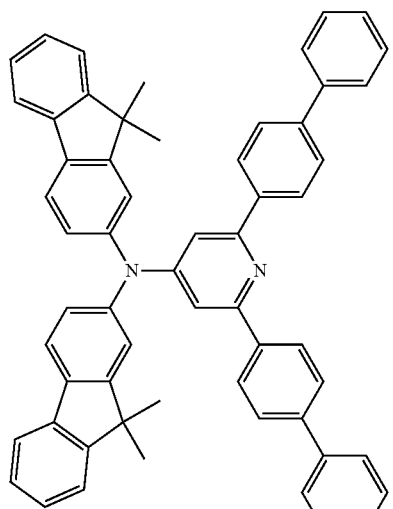
E041
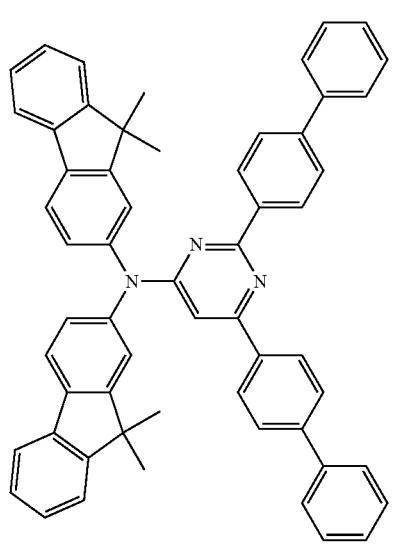
E042
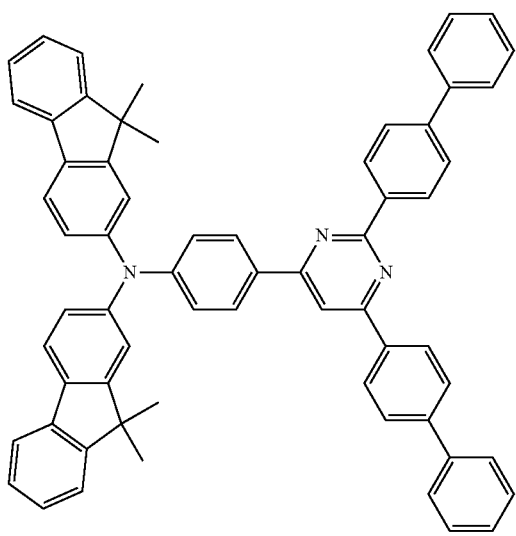
E043
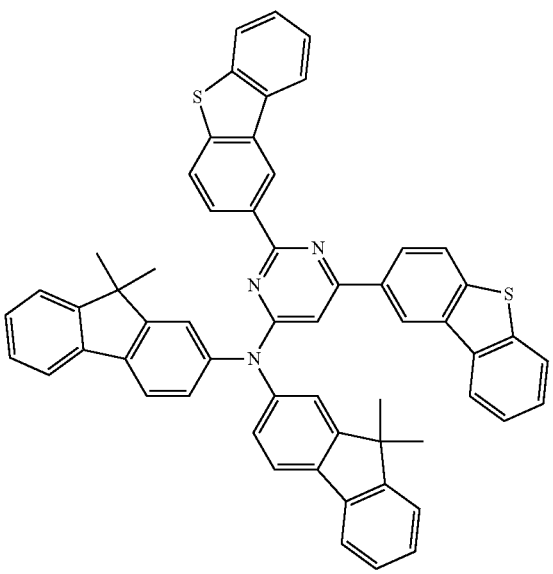
E044
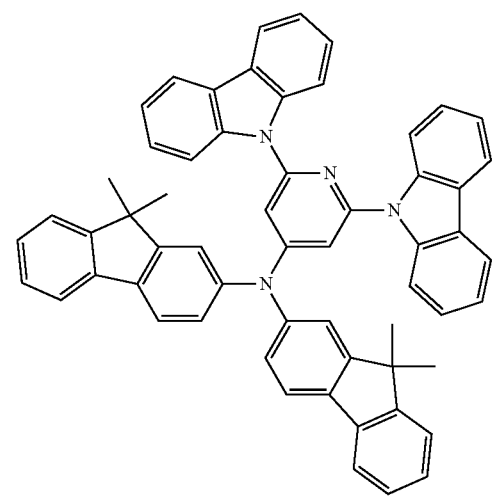
E045
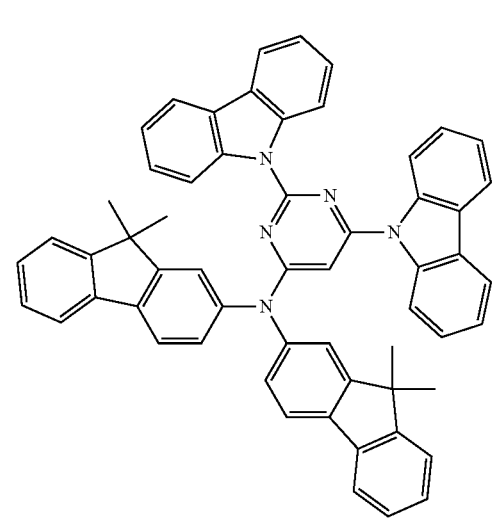

-continued

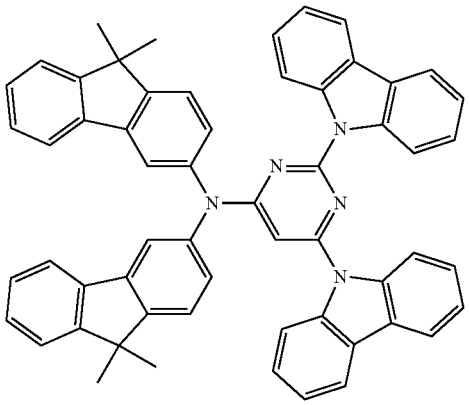
E046

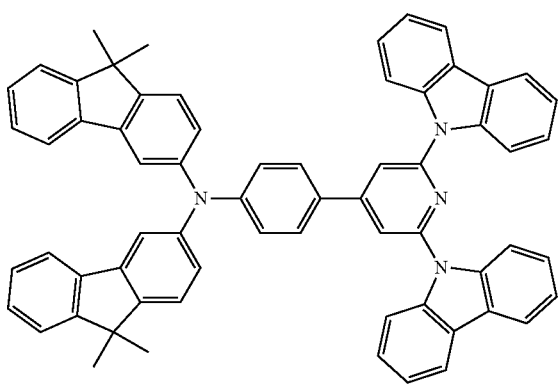
E047

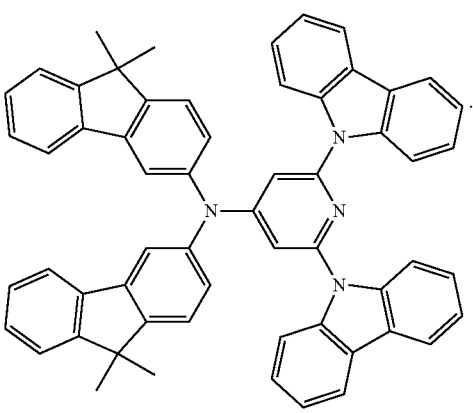
E048

2. The compound according to claim 1, wherein a refractive index n of the compound for a visible light having a wavelength of 400 nm to 700 nm is greater than or equal to 1.9.

3. The compound according to claim 1, wherein an extinction coefficient k of the compound for a visible light having a wavelength of 430 nm to 700 nm is smaller than or equal to 0.0.

4. A display panel comprising an organic light-emitting device, the organic light-emitting device comprising:
an anode;
a cathode disposed oppositely to the anode;
a capping layer disposed at a side of the cathode facing away from anode; and
an organic layer disposed between the anode and the cathode,
wherein the organic layer comprises an electron transmission layer, a hole transmission layer and a light-emitting layer, and the capping layer contains a compound according to claim 1.

5. The display panel according to claim 4, wherein a transmittance of the cathode together with the capping layer for a visible light of 400 to 700 nm is greater than 65%.

6. A display panel comprising an organic light-emitting device, wherein the organic light-emitting device comprises an anode, a cathode disposed oppositely to the anode, a capping layer disposed at a side of the cathode facing away from anode, and an organic layer disposed between the anode and the cathode, the organic layer comprising an electron transmission layer, a hole transmission layer, and a light-emitting layer disposed between the electron transmission layer and the hole transmission layer, the electron transmission layer or the hole transmission layer containing a compound according to claim 1.

7. The display panel according to claim 6, wherein when the electron transmission layer contains the compound, an energy difference between a LUMO energy level of the compound and a LUMO energy level of a light-emitting material of the light-emitting layer adjacent to the electron transmission layer is smaller than 0.2 eV; and a HOMO energy level of the compound is at least 0.3 eV greater than a HOMO energy level of the light-emitting material of the light-emitting layer adjacent to the electron transmission layer.

8. The display panel according claim 7, wherein the organic layer further comprises an electron injection layer adjacent to the electron transmission layer, wherein an energy difference between a LUMO energy level of the compound and a LUMO energy level of an electron injection material of the electron injection layer is smaller than 0.2 eV; and a HOMO energy level of the compound is at least 0.3 eV greater than a HOMO energy level of the electron injection material of the electron injection layer.

9. The display panel according to claim 6, wherein when the hole transmission layer contains the compound, an energy difference between a HOMO energy level of the compound and a HOMO energy level of a light-emitting material of the light-emitting layer adjacent to the hole transmission layer is smaller than 0.2 eV; and a LUMO energy level of the compound is at least 0.3 eV greater than a LUMO energy level of a light-emitting material of the light-emitting layer adjacent to the hole transmission layer.

10. The display panel according to claim 9, wherein the organic layer further comprises a second hole transmission layer adjacent to the hole transmission layer, an energy difference between a HOMO energy level of the compound and a HOMO energy level of a hole transmission material of the second hole transmission layer is smaller than 0.2 eV; and a LUMO energy level of the compound is at least 0.3 eV greater than a LUMO energy level of the hole transmission material of the second hole transmission layer.

* * * * *